US012186007B2

United States Patent
Cho et al.

(10) Patent No.: US 12,186,007 B2
(45) Date of Patent: Jan. 7, 2025

(54) DISPOSABLE END EFFECTORS

(71) Applicant: EndoQuest Robotics, Inc., Houston, TX (US)

(72) Inventors: Sungwoo Cho, Houston, TX (US); Yongman Park, Houston, TX (US); Byeonghui Kim, Seoul (KR); Raymond Lee, Houston, TX (US); Daniel Kim, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 0 days.

(21) Appl. No.: 18/134,426

(22) Filed: Apr. 13, 2023

(65) Prior Publication Data

US 2023/0248419 A1     Aug. 10, 2023

Related U.S. Application Data

(63) Continuation of application No. PCT/US2022/051252, filed on Nov. 29, 2022.

(60) Provisional application No. 63/284,186, filed on Nov. 30, 2021.

(51) Int. Cl.
     *A61B 18/14*      (2006.01)

(52) U.S. Cl.
     CPC .. *A61B 18/1445* (2013.01); *A61B 2018/1457* (2013.01)

(58) Field of Classification Search
     CPC ........ A61B 18/1445; A61B 2018/1457; A61B 34/71
See application file for complete search history.

(56) References Cited

U.S. PATENT DOCUMENTS

| | | | |
|---|---|---|---|
| 5,792,135 A | 8/1998 | Madhani et al. |
| 5,797,900 A | 8/1998 | Madhani et al. |
| 5,836,936 A | 11/1998 | Cuschieri |
| 5,976,122 A | 11/1999 | Madhani et al. |
| 6,063,095 A | 5/2000 | Wang et al. |
| 6,132,368 A | 10/2000 | Cooper |
| 6,162,239 A | 12/2000 | Manhes |
| 6,244,809 B1 | 6/2001 | Wang et al. |
| 6,246,200 B1 | 6/2001 | Blumenkranz et al. |
| 6,312,435 B1 | 11/2001 | Wallace et al. |

(Continued)

FOREIGN PATENT DOCUMENTS

| | | |
|---|---|---|
| CN | 105310775 A | 2/2016 |
| CN | 101978928 B | 5/2016 |

(Continued)

OTHER PUBLICATIONS

Taiwan Intellectual Property Office, Office Action and Search Report issued on Jul. 4, 2023, in corresponding Taiwan Invention Patent Application No. 111145713.

(Continued)

*Primary Examiner* — Linda C Dvorak
*Assistant Examiner* — Ryan T Clark
(74) *Attorney, Agent, or Firm* — Locke Lord LLP; Scott D. Wofsy; Michael J. Pollack

(57) ABSTRACT

An end effector for a minimally invasive medical device can include a base configured to attach to a distal end of a shaft, and a disposable distal portion configured to removably attach to the base to be disposed of after use.

18 Claims, 24 Drawing Sheets

(56) References Cited

U.S. PATENT DOCUMENTS

| | | |
|---|---|---|
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,402,715 B2 | 6/2002 | Manhes |
| 6,424,885 B1 | 7/2002 | Niemeyer et al. |
| 6,441,577 B2 | 8/2002 | Blumenkranz et al. |
| 6,451,027 B1 | 9/2002 | Cooper et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,508,827 B1 | 1/2003 | Manhes |
| 6,522,906 B1 | 2/2003 | Salisbury, Jr. et al. |
| 6,565,554 B1 | 5/2003 | Niemeyer |
| 6,587,750 B2 | 7/2003 | Gerbi et al. |
| 6,645,196 B1 | 11/2003 | Nixon et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,746,443 B1 | 6/2004 | Morley et al. |
| 6,766,204 B2 | 7/2004 | Niemeyer et al. |
| 6,783,524 B2 | 8/2004 | Anderson et al. |
| 6,785,593 B2 | 8/2004 | Wang et al. |
| 6,799,088 B2 | 9/2004 | Wang et al. |
| 6,817,972 B2 | 11/2004 | Snow |
| 6,817,974 B2 | 11/2004 | Cooper et al. |
| 6,836,703 B2 | 12/2004 | Wang et al. |
| 6,837,846 B2 | 1/2005 | Jaffe et al. |
| 6,840,938 B1 | 1/2005 | Morley et al. |
| 6,852,107 B2 | 2/2005 | Wang et al. |
| 6,866,671 B2 | 3/2005 | Tierney et al. |
| 6,871,117 B2 | 3/2005 | Wang et al. |
| 6,892,112 B2 | 5/2005 | Wang et al. |
| 6,905,491 B1 | 6/2005 | Wang et al. |
| 6,951,535 B2 | 10/2005 | Ghodoussi et al. |
| 6,991,627 B2 | 1/2006 | Madhani et al. |
| 6,994,703 B2 | 2/2006 | Wang et al. |
| 7,025,064 B2 | 4/2006 | Wang et al. |
| 7,027,892 B2 | 4/2006 | Wang et al. |
| 7,048,745 B2 | 5/2006 | Tierney et al. |
| 7,066,926 B2 | 6/2006 | Wallace et al. |
| 7,074,179 B2 | 7/2006 | Wang et al. |
| 7,083,571 B2 | 8/2006 | Wang et al. |
| 7,087,049 B2 | 8/2006 | Nowlin et al. |
| 7,090,637 B2 | 8/2006 | Danitz et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,204,844 B2 | 4/2007 | Jensen et al. |
| 7,276,065 B2 | 10/2007 | Morley et al. |
| 7,320,700 B2 | 1/2008 | Cooper et al. |
| 7,326,228 B2 | 2/2008 | Cuschieri et al. |
| 7,331,967 B2 | 2/2008 | Lee et al. |
| 7,333,642 B2 | 2/2008 | Green |
| 7,357,774 B2 | 4/2008 | Cooper |
| 7,398,707 B2 | 7/2008 | Morley et al. |
| 7,524,320 B2 | 4/2009 | Tierney et al. |
| 7,553,277 B2 | 6/2009 | Hoefig et al. |
| 7,574,250 B2 | 8/2009 | Niemeyer |
| 7,608,083 B2 | 10/2009 | Lee et al. |
| 7,615,066 B2 | 11/2009 | Danitz et al. |
| 7,691,098 B2 | 4/2010 | Wallace et al. |
| 7,744,608 B2 | 6/2010 | Lee et al. |
| 7,756,036 B2 | 7/2010 | Druke et al. |
| 7,757,028 B2 | 7/2010 | Druke et al. |
| 7,763,015 B2 | 7/2010 | Cooper et al. |
| 7,780,651 B2 | 8/2010 | Madhani et al. |
| 7,837,674 B2 | 11/2010 | Cooper |
| 7,854,738 B2 | 12/2010 | Lee et al. |
| 7,865,266 B2 | 1/2011 | Moll et al. |
| 7,955,322 B2 | 6/2011 | Devengenzo et al. |
| 7,967,746 B2 | 6/2011 | Leroy et al. |
| 8,052,636 B2 | 11/2011 | Moll et al. |
| 8,054,752 B2 | 11/2011 | Druke et al. |
| 8,068,649 B2 | 11/2011 | Green |
| 8,075,474 B2 | 12/2011 | Honda et al. |
| 8,100,133 B2 | 1/2012 | Mintz et al. |
| 8,120,301 B2 | 2/2012 | Goldberg et al. |
| 8,123,740 B2 | 2/2012 | Madhani et al. |
| 8,147,503 B2 | 4/2012 | Zhao et al. |
| 8,169,468 B2 | 5/2012 | Scott et al. |
| 8,182,415 B2 | 5/2012 | Larkin et al. |
| 8,190,238 B2 | 5/2012 | Moll et al. |
| 8,228,368 B2 | 7/2012 | Zhao et al. |
| 8,323,297 B2 | 12/2012 | Hinman et al. |
| 8,335,590 B2 | 12/2012 | Costa et al. |
| 8,337,521 B2 | 12/2012 | Cooper et al. |
| 8,343,045 B2 | 1/2013 | Swinehart et al. |
| 8,343,141 B2 | 1/2013 | Madhani et al. |
| 8,365,633 B2 | 2/2013 | Simaan et al. |
| 8,375,808 B2 | 2/2013 | Blumenkranz et al. |
| 8,398,541 B2 | 3/2013 | DiMaio et al. |
| 8,437,629 B2 | 5/2013 | McDowall |
| 8,469,947 B2 | 6/2013 | Devengenzo et al. |
| 8,475,366 B2 | 7/2013 | Boulais et al. |
| 8,506,555 B2 | 8/2013 | Ruiz Morales |
| 8,591,399 B2 | 11/2013 | Marescaux et al. |
| 8,594,841 B2 | 11/2013 | Zhao et al. |
| 8,597,280 B2 | 12/2013 | Cooper et al. |
| 8,600,551 B2 | 12/2013 | Itkowitz et al. |
| 8,617,102 B2 | 12/2013 | Moll et al. |
| 8,644,988 B2 | 2/2014 | Prisco et al. |
| 8,679,099 B2 | 3/2014 | Cooper et al. |
| 8,690,908 B2 | 4/2014 | Cooper et al. |
| 8,709,000 B2 | 4/2014 | Madhani et al. |
| 8,740,885 B2 | 6/2014 | Larkin et al. |
| 8,784,435 B2 | 7/2014 | Cooper et al. |
| 8,786,241 B2 | 7/2014 | Nowlin et al. |
| 8,790,243 B2 | 7/2014 | Cooper et al. |
| 8,801,661 B2 | 8/2014 | Moll et al. |
| 8,810,631 B2 | 8/2014 | Scott et al. |
| 8,816,628 B2 | 8/2014 | Nowlin et al. |
| 8,821,480 B2 | 9/2014 | Burbank |
| 8,831,782 B2 | 9/2014 | Itkowitz |
| 8,838,270 B2 | 9/2014 | Druke et al. |
| 8,852,208 B2 | 10/2014 | Gomez et al. |
| 8,878,920 B2 | 11/2014 | Ovod |
| 8,887,595 B2 | 11/2014 | Williams |
| 8,888,690 B2 | 11/2014 | Swinehart et al. |
| 8,888,764 B2 | 11/2014 | Devengenzo et al. |
| 8,903,549 B2 | 12/2014 | Itkowitz et al. |
| 8,918,207 B2 | 12/2014 | Prisco |
| 8,944,070 B2 | 2/2015 | Guthart et al. |
| 8,945,095 B2 | 2/2015 | Blumenkranz et al. |
| 8,998,797 B2 | 4/2015 | Omori |
| 9,011,318 B2 | 4/2015 | Choset et al. |
| 9,050,120 B2 | 6/2015 | Swarup et al. |
| 9,060,678 B2 | 6/2015 | Larkin et al. |
| 9,089,354 B2 | 7/2015 | Simaan et al. |
| 9,095,362 B2 | 8/2015 | Dachs, II et al. |
| 9,107,572 B2 | 8/2015 | Marescaux et al. |
| 9,138,284 B2 | 9/2015 | Krom et al. |
| 9,144,456 B2 | 9/2015 | Rosa et al. |
| 9,173,548 B2 | 11/2015 | Omori |
| 9,179,979 B2 | 11/2015 | Jinno |
| 9,186,221 B2 | 11/2015 | Burbank |
| 9,254,090 B2 | 2/2016 | Watson et al. |
| 9,259,274 B2 | 2/2016 | Prisco |
| 9,259,276 B2 | 2/2016 | Mintz et al. |
| 9,301,807 B2 | 4/2016 | Duval |
| 9,308,937 B2 | 4/2016 | Griffiths et al. |
| 9,339,341 B2 | 5/2016 | Cooper |
| 9,358,074 B2 | 6/2016 | Schena et al. |
| 9,433,342 B2 | 9/2016 | Perretta et al. |
| 9,456,839 B2 | 10/2016 | Cooper |
| 9,486,288 B2 | 11/2016 | Devengenzo et al. |
| 9,498,242 B2 | 11/2016 | Crews et al. |
| 9,504,517 B2 | 11/2016 | Rosa et al. |
| 9,510,915 B2 | 12/2016 | Madhani et al. |
| 9,531,699 B2 | 12/2016 | Panchura et al. |

(56) References Cited

U.S. PATENT DOCUMENTS

| | | |
|---|---|---|
| 9,554,827 B2 | 1/2017 | Omori |
| 9,565,990 B2 | 2/2017 | Lee et al. |
| 9,596,980 B2 | 3/2017 | Marescaux et al. |
| 9,687,310 B2 | 6/2017 | Nowlin et al. |
| 9,717,486 B2 | 8/2017 | Cooper et al. |
| 9,757,149 B2 | 9/2017 | Cooper et al. |
| 9,757,203 B2 | 9/2017 | Hourtash et al. |
| 9,775,678 B2 | 10/2017 | Lohmeier |
| 9,782,056 B2 | 10/2017 | McDowall |
| 9,782,225 B2 | 10/2017 | Lohmeier et al. |
| 9,795,446 B2 | 10/2017 | DiMaio et al. |
| 9,795,453 B2 | 10/2017 | Tierney et al. |
| 9,801,526 B2 | 10/2017 | Larkin et al. |
| 9,801,654 B2 | 10/2017 | Gomez et al. |
| 9,814,527 B2 | 11/2017 | Rogers et al. |
| 9,867,603 B2 | 1/2018 | Merz et al. |
| 9,877,794 B2 | 1/2018 | Csiky |
| 9,901,402 B2 | 2/2018 | Itkowitz et al. |
| 9,918,659 B2 | 3/2018 | Chopra et al. |
| 9,949,620 B2 | 4/2018 | Duval et al. |
| 9,962,066 B2 | 5/2018 | Rogers et al. |
| 9,968,405 B2 | 5/2018 | Cooper et al. |
| 9,980,630 B2 | 5/2018 | Larkin et al. |
| 10,010,331 B2 | 7/2018 | Morash |
| 10,039,473 B2 | 8/2018 | Zhao et al. |
| 10,058,390 B2 | 8/2018 | Simaan et al. |
| 10,085,788 B2 | 10/2018 | Privitera et al. |
| 10,085,806 B2 | 10/2018 | Hagn et al. |
| 10,092,172 B2 | 10/2018 | Peh et al. |
| 10,105,128 B2 | 10/2018 | Cooper et al. |
| 10,117,715 B2 | 11/2018 | Lohmeier et al. |
| 10,159,536 B2 | 12/2018 | Kralicky et al. |
| 10,178,368 B2 | 1/2019 | Zhao et al. |
| 10,179,024 B2 | 1/2019 | Yeung |
| 10,179,413 B2 | 1/2019 | Rockrohr |
| 10,188,472 B2 | 1/2019 | Diolaiti et al. |
| 10,258,421 B2 | 4/2019 | Lohmeier et al. |
| 10,278,782 B2 | 5/2019 | Jarc et al. |
| 10,321,964 B2 | 6/2019 | Grover et al. |
| 10,327,856 B2 | 6/2019 | Kralicky et al. |
| 10,363,107 B2 | 7/2019 | Blumenkranz et al. |
| 10,365,295 B2 | 7/2019 | Blumenkranz et al. |
| 10,390,687 B2 | 8/2019 | Choi et al. |
| 10,390,895 B2 | 8/2019 | Henderson et al. |
| 10,391,635 B2 | 8/2019 | Berghofer et al. |
| 10,398,520 B2 | 9/2019 | Larkin et al. |
| 10,413,370 B2 | 9/2019 | Yates et al. |
| 10,448,813 B2 | 10/2019 | Cooper et al. |
| 10,456,166 B2 | 10/2019 | Cooper et al. |
| 10,507,068 B2 | 12/2019 | Kopp et al. |
| 10,512,481 B2 | 12/2019 | Cooper |
| 10,524,644 B2 | 1/2020 | Scott et al. |
| 10,524,868 B2 | 1/2020 | Cooper et al. |
| 10,531,929 B2 | 1/2020 | Widenhouse et al. |
| 10,602,958 B2 | 3/2020 | Silverstein et al. |
| 10,646,990 B2 | 5/2020 | Olds et al. |
| 10,660,713 B2 | 5/2020 | McCrea et al. |
| 10,682,193 B2 | 6/2020 | Choi et al. |
| 10,729,503 B2 | 8/2020 | Cameron |
| 10,736,702 B2 | 8/2020 | Harris et al. |
| 10,779,896 B2 | 9/2020 | Dachs, II et al. |
| 10,779,899 B2 | 9/2020 | Griffiths et al. |
| 10,786,329 B2 | 9/2020 | Schuh et al. |
| 10,820,953 B2 | 11/2020 | Kralicky et al. |
| 10,828,115 B2 | 11/2020 | Koenig et al. |
| 10,828,117 B2 | 11/2020 | Evans |
| 10,835,331 B2 | 11/2020 | Burbank |
| 10,835,335 B2 | 11/2020 | Perdue et al. |
| 10,856,946 B2 | 12/2020 | Solomon et al. |
| 10,864,051 B2 | 12/2020 | Simi et al. |
| 10,874,475 B2 | 12/2020 | Iceman |
| 10,881,422 B2 | 1/2021 | Kim et al. |
| 10,898,189 B2 | 1/2021 | McDonald, II |
| 10,898,281 B2 | 1/2021 | Cooper et al. |
| 10,905,505 B1 | 2/2021 | Barakat et al. |
| 10,918,449 B2 | 2/2021 | Solomon et al. |
| 10,939,970 B2 | 3/2021 | Laakso et al. |
| 10,959,607 B2 | 3/2021 | Rogers et al. |
| 2002/0161281 A1 | 10/2002 | Jaffe et al. |
| 2003/0036748 A1 | 2/2003 | Cooper et al. |
| 2003/0083673 A1 | 5/2003 | Tierney et al. |
| 2003/0114962 A1 | 6/2003 | Niemeyer |
| 2003/0135203 A1 | 7/2003 | Wang et al. |
| 2004/0049205 A1 | 3/2004 | Lee et al. |
| 2004/0138700 A1 | 7/2004 | Cooper et al. |
| 2004/0162547 A1 | 8/2004 | Wallace et al. |
| 2004/0236316 A1 | 11/2004 | Danitz et al. |
| 2005/0043718 A1 | 2/2005 | Madhani et al. |
| 2005/0059960 A1 | 3/2005 | Simaan et al. |
| 2005/0149003 A1 | 7/2005 | Tierney et al. |
| 2005/0200324 A1 | 9/2005 | Guthart et al. |
| 2005/0204851 A1 | 9/2005 | Morley et al. |
| 2005/0216033 A1 | 9/2005 | Lee et al. |
| 2005/0251112 A1 | 11/2005 | Danitz et al. |
| 2006/0152516 A1 | 7/2006 | Plummer |
| 2006/0167440 A1 | 7/2006 | Cooper et al. |
| 2007/0043338 A1 | 2/2007 | Moll et al. |
| 2007/0137372 A1 | 6/2007 | Devengenzo et al. |
| 2007/0151390 A1 | 7/2007 | Blumenkranz et al. |
| 2007/0156119 A1 | 7/2007 | Wallace et al. |
| 2007/0156122 A1 | 7/2007 | Cooper |
| 2007/0197896 A1 | 8/2007 | Moll et al. |
| 2007/0244515 A1 | 10/2007 | Fanous |
| 2008/0065105 A1 | 3/2008 | Larkin et al. |
| 2008/0065107 A1 | 3/2008 | Larkin et al. |
| 2008/0065111 A1 | 3/2008 | Blumenkranz et al. |
| 2008/0071291 A1 | 3/2008 | Duval et al. |
| 2008/0077159 A1 | 3/2008 | Madhani et al. |
| 2008/0177282 A1 | 7/2008 | Lee et al. |
| 2008/0177284 A1 | 7/2008 | Lee et al. |
| 2008/0269562 A1 | 10/2008 | Marescaux et al. |
| 2008/0287963 A1 | 11/2008 | Rogers et al. |
| 2009/0023989 A1 | 1/2009 | Honda et al. |
| 2009/0171151 A1 | 7/2009 | Choset et al. |
| 2009/0192519 A1 | 7/2009 | Omori |
| 2009/0216225 A1 | 8/2009 | Ben-Nun |
| 2010/0011901 A1 | 1/2010 | Burbank |
| 2010/0048999 A1 | 2/2010 | Boulais et al. |
| 2010/0082041 A1 | 4/2010 | Prisco |
| 2010/0234831 A1 | 9/2010 | Hinman et al. |
| 2010/0274087 A1 | 10/2010 | Diolaiti et al. |
| 2010/0292708 A1 | 11/2010 | Madhani et al. |
| 2011/0118755 A1 | 5/2011 | Cooper et al. |
| 2011/0125166 A1 | 5/2011 | Cooper et al. |
| 2011/0144658 A1 | 6/2011 | Wenderow et al. |
| 2011/0152879 A1 | 6/2011 | Williams |
| 2011/0196419 A1 | 8/2011 | Cooper |
| 2011/0277580 A1 | 11/2011 | Cooper et al. |
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0123800 A1 | 5/2013 | Leroy et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257336 A1 | 9/2014 | Choi et al. |
| 2014/0277106 A1 | 9/2014 | Crews et al. |
| 2014/0296637 A1 | 10/2014 | Lee et al. |

(56) References Cited

U.S. PATENT DOCUMENTS

| | | |
|---|---|---|
| 2014/0296872 A1 | 10/2014 | Cooper et al. |
| 2015/0066002 A1 | 3/2015 | Cooper et al. |
| 2015/0100066 A1 | 4/2015 | Kostrzewski et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |
| 2016/0015447 A1 | 1/2016 | Rosa et al. |
| 2016/0058512 A1 | 3/2016 | Gomez et al. |
| 2016/0066773 A1 | 3/2016 | Cooper et al. |
| 2016/0175060 A1* | 6/2016 | Park ............ A61B 17/00 606/130 |
| 2016/0242860 A1 | 8/2016 | Diolaiti et al. |
| 2016/0256183 A1 | 9/2016 | Cooper |
| 2017/0014197 A1 | 1/2017 | McCrea et al. |
| 2017/0020615 A1 | 1/2017 | Koenig et al. |
| 2017/0071628 A1 | 3/2017 | Cooper et al. |
| 2017/0112505 A1 | 4/2017 | Morash |
| 2017/0156804 A1 | 6/2017 | Cooper et al. |
| 2017/0202569 A1 | 7/2017 | Roop et al. |
| 2017/0265923 A1 | 9/2017 | Privitera et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Innell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Arkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | Mcdonald, II |
| 2018/0318023 A1 | 11/2018 | Griffiths et al. |
| 2018/0353204 A1 | 12/2018 | Solomon et al. |
| 2018/0370045 A1 | 12/2018 | Kan |
| 2019/0000460 A1 | 1/2019 | Shelton, IV et al. |
| 2019/0039241 A1 | 2/2019 | Langenfeld et al. |
| 2019/0117247 A1 | 4/2019 | Kim et al. |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0314645 A1 | 10/2019 | Ciresianu et al. |
| 2019/0328472 A1 | 10/2019 | Tojo et al. |
| 2019/0380801 A1 | 12/2019 | Savall et al. |
| 2020/0038123 A1 | 2/2020 | Graetzel et al. |
| 2020/0069389 A1 | 3/2020 | Morrissette et al. |
| 2020/0107898 A1 | 4/2020 | Kim et al. |
| 2020/0146763 A1 | 5/2020 | Schena et al. |
| 2020/0179067 A1 | 6/2020 | Ross et al. |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0315645 A1 | 10/2020 | Kim et al. |
| 2020/0330173 A1 | 10/2020 | Kapadia et al. |
| 2020/0367979 A1 | 11/2020 | Aakso et al. |
| 2020/0397456 A1 | 12/2020 | Kim et al. |
| 2020/0397457 A1 | 12/2020 | Kim et al. |
| 2021/0022818 A1 | 1/2021 | Tsuji et al. |
| 2021/0045819 A1 | 2/2021 | Castillo et al. |
| 2021/0161606 A1 | 6/2021 | Hares et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0275266 A1 | 9/2021 | Kim et al. |
| 2021/0322045 A1 | 10/2021 | Kim et al. |
| 2021/0322046 A1 | 10/2021 | Kim et al. |
| 2021/0338052 A1 | 11/2021 | Ouyang et al. |
| 2022/0354524 A1 | 11/2022 | Kim et al. |
| 2023/0210618 A1 | 7/2023 | Kim et al. |
| 2023/0210621 A1 | 7/2023 | Noh et al. |
| 2023/0248450 A1 | 8/2023 | Ravi et al. |
| 2023/0248457 A1 | 8/2023 | Lee et al. |
| 2023/0255702 A1 | 8/2023 | Park et al. |
| 2023/0285090 A1 | 9/2023 | Lee et al. |
| 2023/0285098 A1 | 9/2023 | Lee et al. |
| 2023/0285099 A1 | 9/2023 | Lee et al. |
| 2023/0355221 A1 | 11/2023 | Shin et al. |
| 2023/0363842 A1 | 11/2023 | Choi et al. |
| 2023/0363847 A1 | 11/2023 | Lee et al. |
| 2024/0058079 A1 | 2/2024 | Kim et al. |

FOREIGN PATENT DOCUMENTS

| | | |
|---|---|---|
| CN | 108309370 A | 7/2018 |
| CN | 109674647 A | 4/2019 |
| CN | 109925051 A | 6/2019 |
| CN | 213606867 U | 7/2021 |
| EP | 0380874 A1 | 8/1990 |
| EP | 2968048 B1 | 6/2018 |
| EP | 3175813 B1 | 1/2020 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| WO | 02080793 A1 | 10/2002 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

"Plenary 1: Colubris MX"—YouTube Video link address https://www.youtube.com/watch?v=in_IuQiAZg8 dated Aug. 20, 2020.

International Search Report and Written Opinion, of the Korean Intellectual Property Office, as ISA, mailed Apr. 6, 2023, in corresponding International Patent Application PCT/US2022/051217.

International Search Report and Written Opinion, of the Korean Intellectual Property Office, as ISA, mailed Apr. 6, 2023, in corresponding International Patent Application PCT/US2022/051220.

International Search Report and Written Opinion, of the Korean Intellectual Property Office, as ISA, mailed Apr. 7, 2023, in corresponding International Patent Application PCT/US2022/051225.

International Search Report and Written Opinion, of the Korean Intellectual Property Office, as ISA, mailed Apr. 6, 2023, in corresponding International Patent Application PCT/US2022/051237.

International Search Report and Written Opinion, of the Korean Intellectual Property Office, as ISA, mailed Apr. 6, 2023, in corresponding International Patent Application PCT/US2022/051246.

International Search Report and Written Opinion, of the Korean Intellectual Property Office, as ISA, mailed Apr. 6, 2023, in corresponding International Patent Application PCT/US2022/051255.

International Search Report and Written Opinion, of the Korean

(56) References Cited

OTHER PUBLICATIONS

Intellectual Property Office, as ISA, mailed Apr. 6, 2023, in corresponding International Patent Application PCT/US2022/051259.
International Search Report and Written Opinion, of the Korean Intellectual Property Office, as ISA, mailed Apr. 6, 2023, in corresponding International Patent Application PCT/US2022/051261.
International Search Report and Written Opinion, of the Korean Intellectual Property Office, as ISA, mailed Apr. 14, 2023, in corresponding International Patent Application PCT/US2022/051265.
International Search Report and Written Opinion, of the Korean Intellectual Property Office, as ISA, mailed Apr. 6, 2023, in corresponding International Patent Application PCT/US2022/051262.
International Search Report and Written Opinion, of the Korean Intellectual Property Office, as ISA, mailed Aug. 7, 2023, in corresponding International Patent Application PCT/US2022/051252.

* cited by examiner

DISPOSABLE END EFFECTORS

CROSS-REFERENCE TO RELATED APPLICATIONS

This application is a continuation of International Patent Application No. PCT/US2022/051252 filed Nov. 29, 2022, which claims priority to and the benefit of U.S. Provisional Application No. 63/284,186, filed Nov. 30, 2021, the entire contents of which are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, an end effector for a minimally invasive medical device can include a base configured to attach to a distal end of a shaft, and a disposable distal portion configured to removably attach to the base to be disposed of after use. The disposable distal portion can include an electrically conductive material for an electrosurgical procedure. The disposable distal portion can be electrically connected to the base when removably attached to the base, for example.

The distal portion can be or can include blades or jaws including a conductive material to provide electrosurgical energy to tissue. In certain embodiments, the disposable distal portion can include a non-conductive clevis, e.g., which can include or be made of an electrically non-conductive material. The blades or jaws can be mounted to the non-conductive clevis to pivot about a pivot joint of the clevis.

The base can include a base connection assembly configured to mechanically and electrically connect the base to the blades or jaws. In certain embodiments, the base connection assembly can include a non-conductive center post configured to mechanically connect the blades or jaws to actuate the blades or jaws between an open and a closed position.

In certain embodiments, the base can include a threaded portion proximal to the base connection assembly. The disposable distal portion can include a mating collar configured to mesh with the threaded portion of the base. In certain embodiments, the mating collar can be configured to rotate relative to the clevis to install the clevis to the base. The mating collar can axially retain the clevis to the base when attached to the threaded portion. Any other suitable connection type is contemplated herein.

In certain embodiments, when the disposable distal portion is installed on the base, the electrical pathway through the blades or jaws is insulated by the non-conductive clevis and non-conductive center post are in contact with at least a portion of the disposable distal portion to form an electrical energy insulation therebetween such that no insulating sheath is required to be installed over the base and/or the disposable distal portion. In certain embodiments, a sheath may still be used if desired.

The base can be configured to connect to a distal end of a steerable shaft of a robotically controlled medical device. The base can include a guide portion (e.g. a pulley) configured to be connected to the actuation component via an actuator wire to control a position of the blades or jaws. Any other suitable mechanical arrangement (e.g., a spool, a roller) is contemplated herein.

In accordance with at least one aspect of this disclosure, the distal portion can include a mount portion configured to abut the base, and a clevis connected to the mount portion. The blades or jaws can be mounted to the clevis to pivot about a pivot joint of the clevis.

The base can be configured to removably mechanically engage the blades or jaws to actuate the blades or jaws. The base can include a drive structure configured to mechanically engage the blades or jaws to actuate the blades or jaws between an open and a closed position.

The disposable distal portion and the base can be configured to be selectively axially retained together by a locking sleeve. The system can further include the locking sleeve configured to selectively lock the disposable distal portion to the base.

The base can include one or more locking channels. The disposable distal portion can include one or more alignment channels defined through a lip thereof. The locking sleeve can include a plurality of lock protrusions on an inner surface thereof. For example, one or more proximal lock protrusions can be configured to be axially advanced through the alignment channels to a position beyond the lip and rotated into a respective locking channel of the base. Also, one or more distal inner stop protrusions can be configured to axially engage the lip to limit axial advancement of the sleeve and to retain the disposable distal portion to the base when the sleeve is rotated into a locked position such that the one or more proximal lock protrusions are within the one or more locking channels.

In certain embodiments, the base can include a base clevis and an actuation assembly connected to the base clevis and the drive structure to actuate the drive structure relative to the base clevis. The actuation assembly can include an actuator housing connected to the drive structure and a pulley assembly within the actuator housing and configured to move the actuator housing relative to the base clevis.

In certain embodiments, the pulley assembly can include a pulley and an anchor. The pulley can be pinned to the base clevis via a pulley pin. The pulley pin can be disposed within an axial slot of the actuator housing to allow the actuator housing to axially slide relative to the pulley. The anchor can be configured to move relative to the pulley between an open position of the blades or jaws and a closed position of the blades or jaws. The anchor can be slideably connected via an anchor pin to the actuator housing at a radial slot to translate relative to the actuator housing in a radial direction orthogonal to the axial direction. In certain embodiments, the base clevis can include a diagonal slot configured to guide the anchor pin within the radial slot as the actuator housing moves axially relative to the base clevis.

The anchor can be configured to retain a first end of a first wire that is wrapped around the pulley. The anchor can be configured to retain a second end of a second wire (which can be the same wire as the first wire, or can be a different wire) such that pulling actuation on the first wire brings the anchor closer to the pulley thereby distally actuating the actuator housing, and pulling actuation on the second wire separates the pulley and the anchor thereby proximally actuating the actuator housing.

In certain embodiments, the base clevis can be configured to abut the mount portion and to orient the mount portion rotationally relative to the base (e.g., with one or more mount keys). In certain embodiments, the mount portion and the base clevis can include (e.g., be made of) a non-conductive material. In certain embodiments, the actuator housing can include (e.g., made of) a non-conductive material. The drive structure can be include, e.g., be made of, a conductive material and can be configured to electrically connect to an electrical wire (e.g., mounted in a wire channel. The drive structure can be attached to the actuator housing in any suitable manner (e.g., via a non-conductive core member).

In accordance with at least one aspect of this disclosure, a medical device can include an adapter configured to connect to and be actuated by a robotic surgical system, an elongate member extending from the adapter, the elongate member configured to be positioned as a function of the actuation of the adapter, and an end effector connected to the elongate member. The end effector can be any suitable embodiment of an end effector as disclosed herein, e.g., as described above.

In accordance with at least one aspect of this disclosure a method for operating an end effector for a minimally invasive medical device can include using an end effector in a medical procedure, detaching a first disposable distal portion of the end effector from a base of the end effector, and attaching a second disposable distal portion to the base of the end effector to replace the first distal portion. In certain embodiments, the method can include reusing the end effector having the second disposable distal portion in another medical procedure. The method can include any other suitable method(s) and/or portion(s) thereof.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
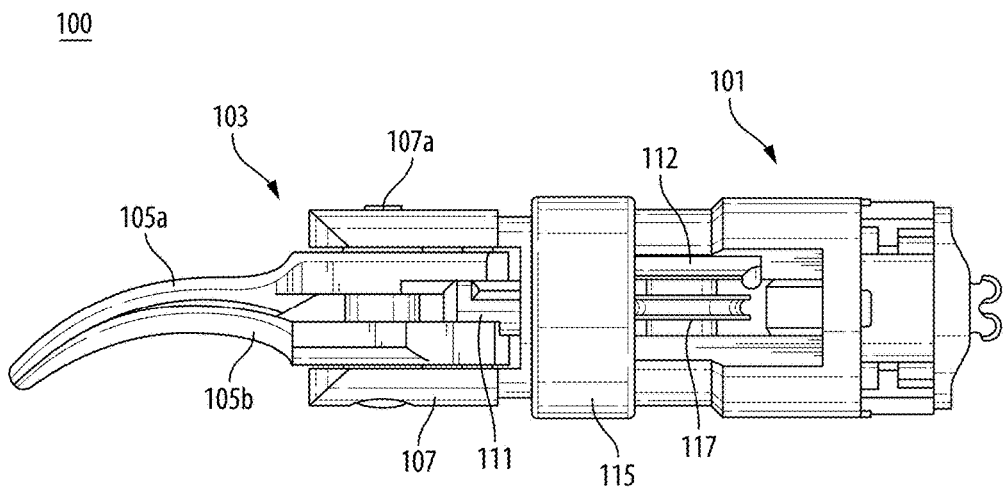
FIG. 1 is an elevation view of an embodiment of an end effector in accordance with this disclosure.

Reference will now be made to the drawings wherein like reference numerals identify similar structural features or aspects of the subject disclosure. For purposes of explanation and illustration, and not limitation, an illustrative view of an embodiment of an end effector in accordance with the disclosure is shown in FIG. 1 and is designated generally by reference character 100. Other embodiments and/or aspects of this disclosure are shown in FIGS. 2-14.

Figure 2:
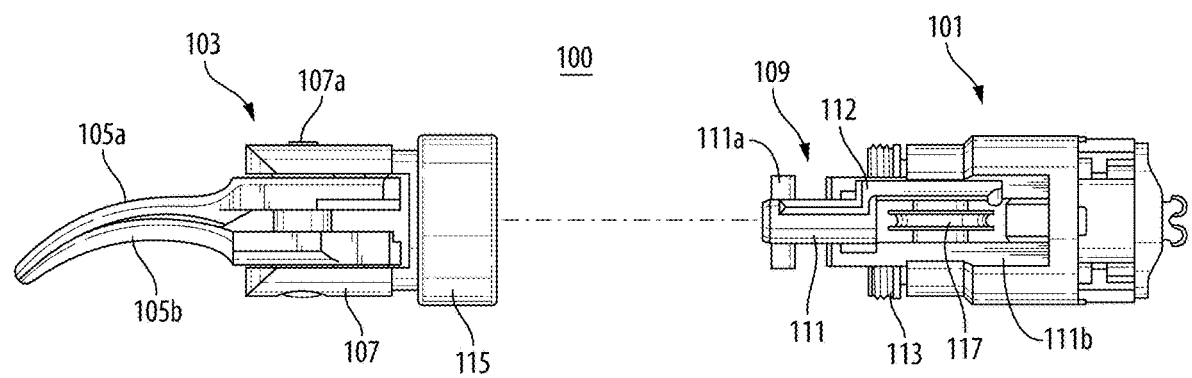
FIG. 2 is an exploded elevation view of an embodiment of an end effector in accordance with this disclosure.
Figure 3:
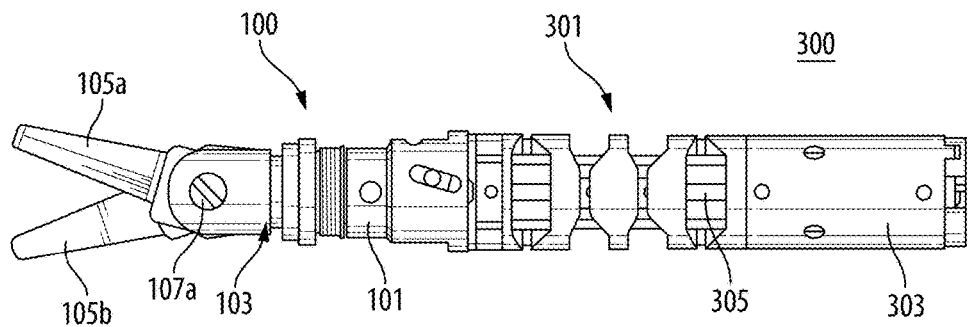
FIG. 3 is an embodiment of distal end of a steerable shaft having the embodiment of an end effector of FIGS. 1 and 2 attached thereto.
Figure 4A:
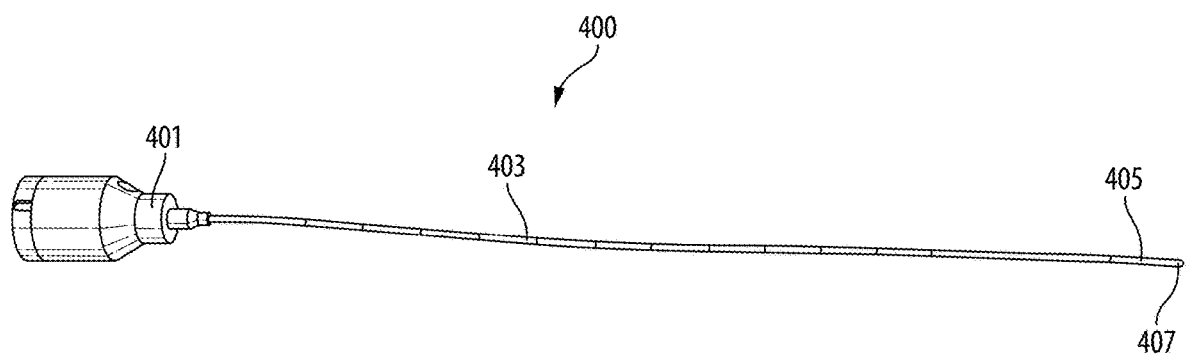
FIG. 4A shows a perspective view of an embodiment of a monopolar energy surgical instrument in accordance with this disclosure.
Figure 4B:
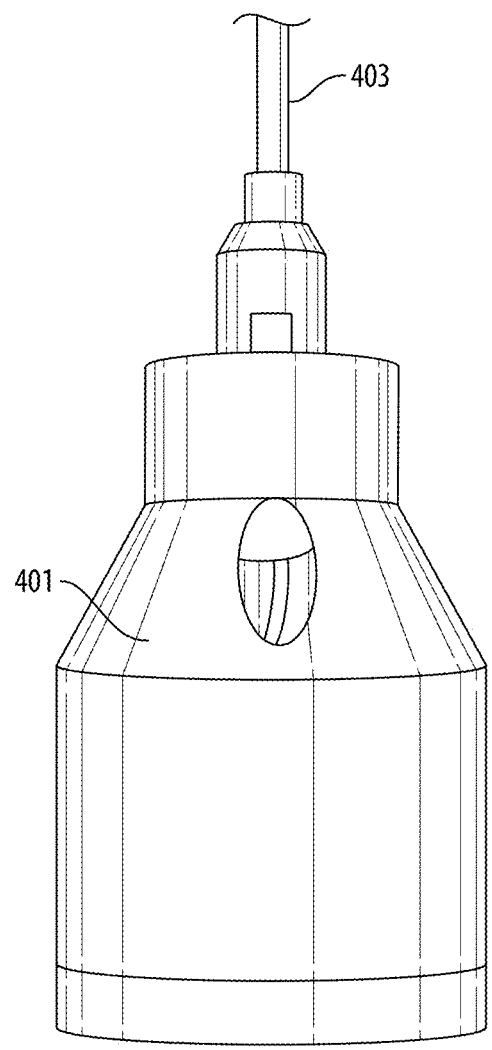
FIG. 4B shows a partial plan view of the embodiment of FIG. 4A.
Figure 4C:
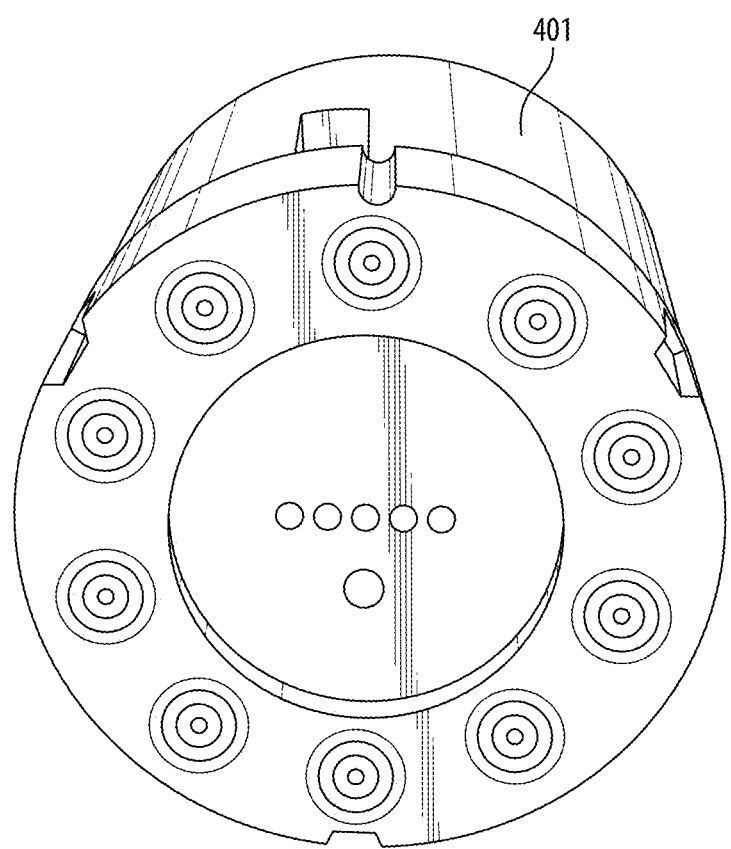
FIG. 4C shows a partial proximal elevation view of the embodiment of FIG. 4A.
Figure 4D:
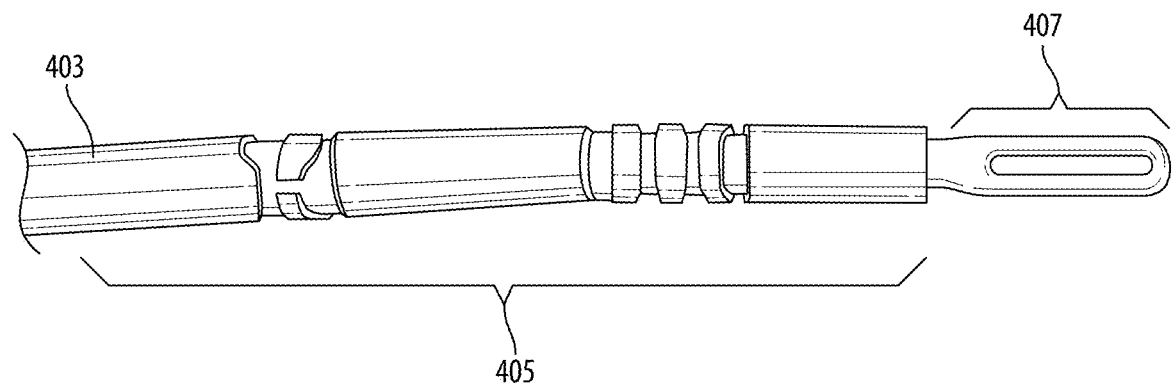
FIG. 4D shows a partial distal view of the embodiment of FIG. 4A, showing a distal end of a shaft having one or more segments and an end effector.

In accordance with at least one aspect of this disclosure, referring to FIGS. 1, 2, and 3, an end effector 100 for a minimally invasive medical device (e.g., a robotically controlled steerable device 300 as shown in FIG. 3) including a base 101 configured to attach to a distal end 303 of a shaft 301, and a disposable distal portion 103 configured to removably attach to the base 101 to be disposed of after use (e.g., a single use). The base 101 can be configured to be reused (e.g., a limited number of times) and/or autoclaved to be cleaned. The embodiment of FIGS. 1, 2, and 3 can be an end effector of an energy surgical instrument for robotic surgical systems.

The disposable distal portion 103 can be or can include a pair of scissor-like blades 105a, 105b or jaws for cooperatively shearing the tissue. The disposable distal portion 103 can include an insulated conductor 305 extending longitudinally from a proximal end 402 of the shaft 301 to the distal end 303 thereof to electrically communicate with at least a portion of the base connection assembly 109 (e.g. a slide post (or pin) 111a, which is detailed below). In certain embodiments, at least a portion of the base 101, the disposable distal portion 103, and blades 105a, 105b or jaws can comprise conductive materials, such as stainless steel and the like, so as to provide a conduction path when the disposable distal portion 103 is electrically connected to the base 101. In certain embodiments, the disposable distal portion 103 can include a non-conductive clevis 107, e.g., which can be made of an electrically non-conductive material (e.g., plastic, ceramic). The blades 105a, b or jaws can be mounted to the non-conductive clevis 107 to pivot about a pivot joint 107a of the clevis 107.

As shown in FIG. 2, the base 101 can include a base connection assembly 109 configured to mechanically and electrically connect the base 101 to the scissors 105a, 105b or jaws. In certain embodiments, the base connection assembly 109 can include a non-conductive center post 111 configured to mechanically connect the blades 105a, 105b or jaws to an actuation component (e.g., the slide post 111a, connected to an actuation mechanism 111b (for example, a moveable frame connected to the slide post 111a) which is slidably housed within the base 101) to actuate the blades 105a, 105b or jaws between an open position (e.g., as shown in FIG. 3) and a closed position (e.g., as shown in FIGS. 1 and 2). For example, when the actuation mechanism 111b and the slide post 111a slide proximally toward to the proximal end of the shaft 301, the blades 105a, 105b close upon one another in a shearing action. As the actuation mechanism 111b and the slide post 111a slide distally toward the disposable distal portion 103, the blades 105a, 105b open apart from one another, as show in FIG. 3. Any other suitable actuation tool/mechanism is contemplated herein. A conductive distal end 112 of insulated conductor 305 can be mounted to the non-conductive center post 111 for providing electrosurgical energy to the scissors 105a, 105b or jaws.

In certain embodiments, the base 101 can include a threaded portion 113 proximal to the base connection assembly 109. The disposable distal portion 103 can include a mating collar 115 configured to mesh with the threaded portion 113 of the base 101. In certain embodiments, the mating collar 115 can be configured to rotate relative to the clevis 107 to install the clevis 107 to the base 101. The mating collar 115 can axially retain the clevis 107 to the base 101 when attached to the threaded portion 113. Any other suitable connection type is contemplated herein.

In certain embodiments, when the disposable distal portion 103 is installed on the base 101, the non-conductive clevis 107 and non-conductive center post 111 are in contact with at least a portion of the disposable distal portion 103 to form an electrical energy insulation therebetween, and thereby the electrical pathway (or conduction path) through the blades 105a, 105b or jaws can be insulated such that no additional insulating sheath is required to be installed over the base 101 and/or the disposable distal portion 103. In certain embodiments, a sheath may still be used if desired.

The base 101 can be configured to connect to a distal end of a steerable shaft 301, e.g., as shown in FIG. 3, of a robotically controlled medical device. The base 101 can include a guide portion (e.g. a pulley 117) configured to be connected to the actuation component via an actuator wire (not shown) to control a position of the slide post 111a, the actuation mechanism 111b, the blades 105a, 105b or jaws.

Any other suitable mechanical arrangement (e.g., such as, but not limited to a spool, a roller, or similar) is contemplated herein.

Embodiments can include a monopolar curved scissors or other suitable jaw device designed for electrical energy insulation. Embodiments can also include distal scissors blades that are designed to be disposable to maximize cutting performance, for example. Any other suitable disposable component/end effector is contemplated herein.

Traditional monopolar curved scissors are designed and insulated with an instrument sheath, which poses a risk of leakage of energy during operation. Embodiments can provide solutions to this issue, as well as reusability of the medical device assembly except for the distal end portion.

Referring to FIGS. 4A-4D, an embodiment of a medical device, e.g., a monopolar energy surgical instrument 400, is provided. The monopolar energy surgical instrument 400 can include an instrument adapter 401, a flexible, elongated shaft 403 (e.g., similar as described above with respect to the shaft 301) having a proximal end 402 extending from the instrument adapter 401, one or more (e.g., a plurality) of bending segments 405 provided at the distal end of the flexible, elongated shaft 403, and an end effector 407 (e.g., which can be the same or similar as described hereinabove or below with respect to end effector 100, 500) adjacent to a distal segment of the bending segments 405. The instrument adapter 401 can include one or more flush ports (used for instrument reprocessing) and a monopolar cable plug that allows a monopolar cable (not shown) to be plugged into this connection interface, thereby electrically connecting to the monopolar energy surgical instrument 400.

Figure 5A:
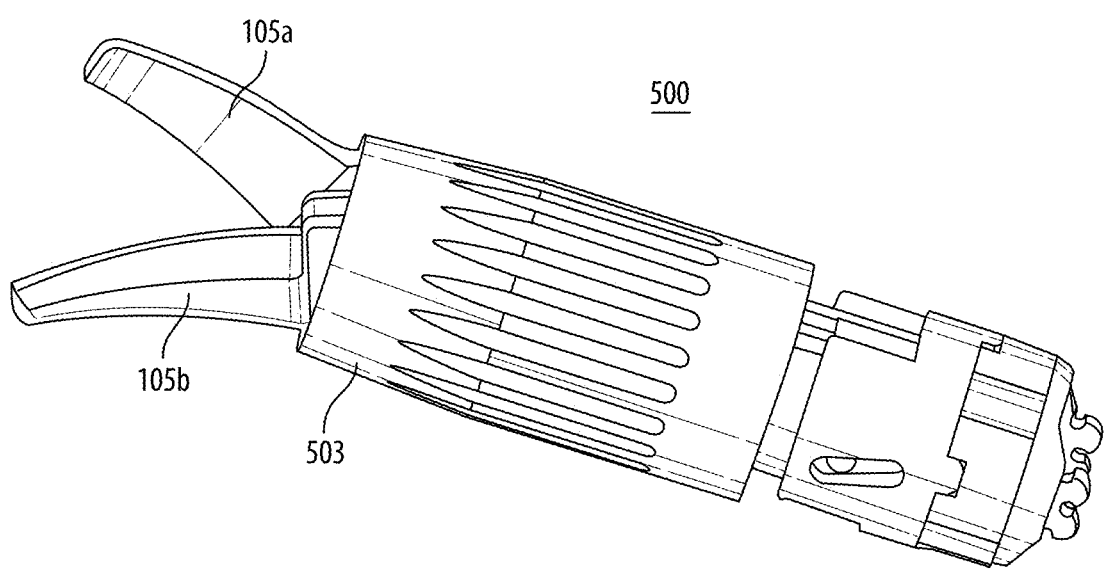
FIG. 5A is a perspective view of another embodiment of an end effector in accordance with this disclosure.

Referring to FIGS. 5A-13C, another embodiment of an end effector 500 is illustrated. FIG. 5A shows a perspective view of another embodiment of an end effector in accordance with this disclosure. FIG. 5B is a perspective view of the embodiment of FIG. 5A, showing a mechanical assembly 501 having the locking sleeve 503 removed. The mechanical assembly 501 can be formed by a disposable distal portion 501a (e.g., a distal assembly as shown) and a base 501b (e.g., a proximal assembly as shown), for example.

Figure 5B:
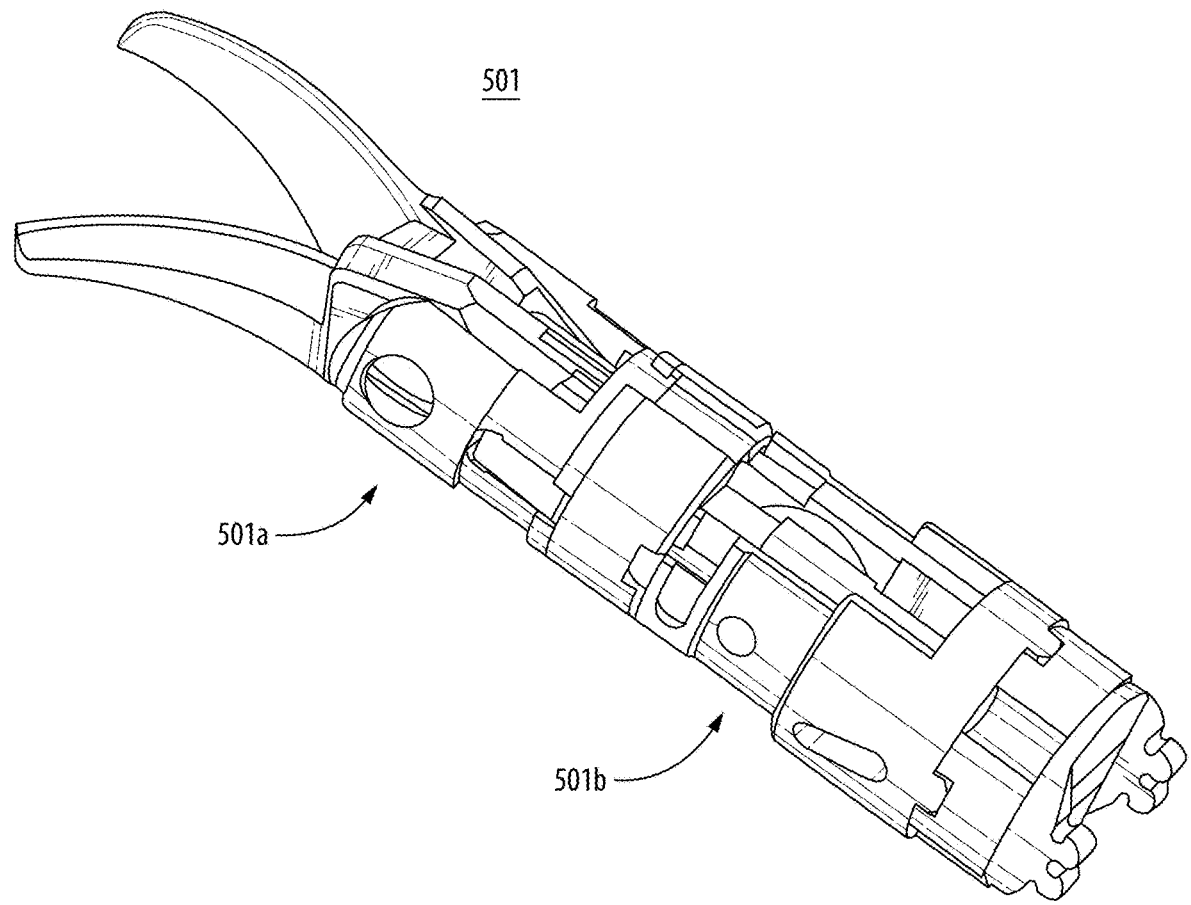
FIG. 5B is a perspective view of the embodiment of FIG. 5A, showing a mechanical assembly having the locking sleeve removed, the mechanical assembly being formed by a disposable distal portion and a base.
Figure 6A:
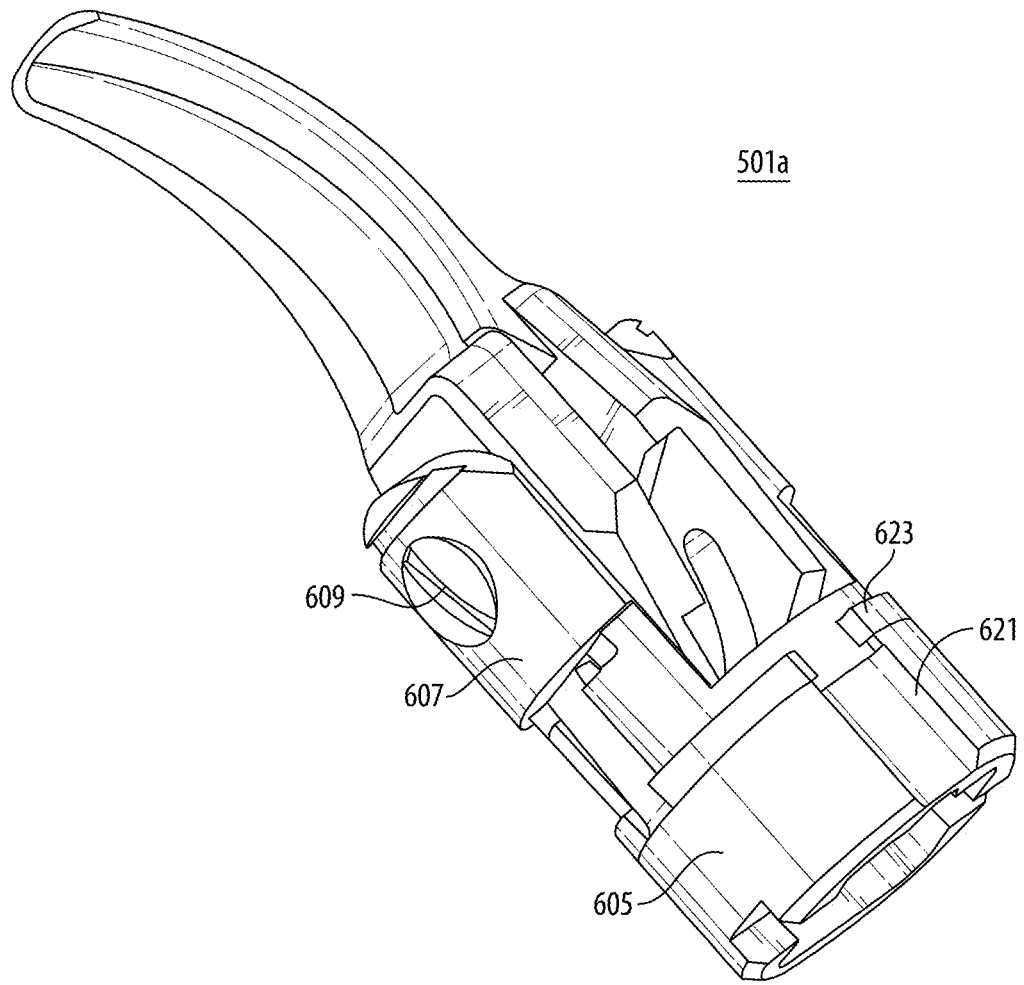
FIG. 6A is a perspective view of a disposable distal portion of the embodiment of FIG. 5.
Figure 6B:
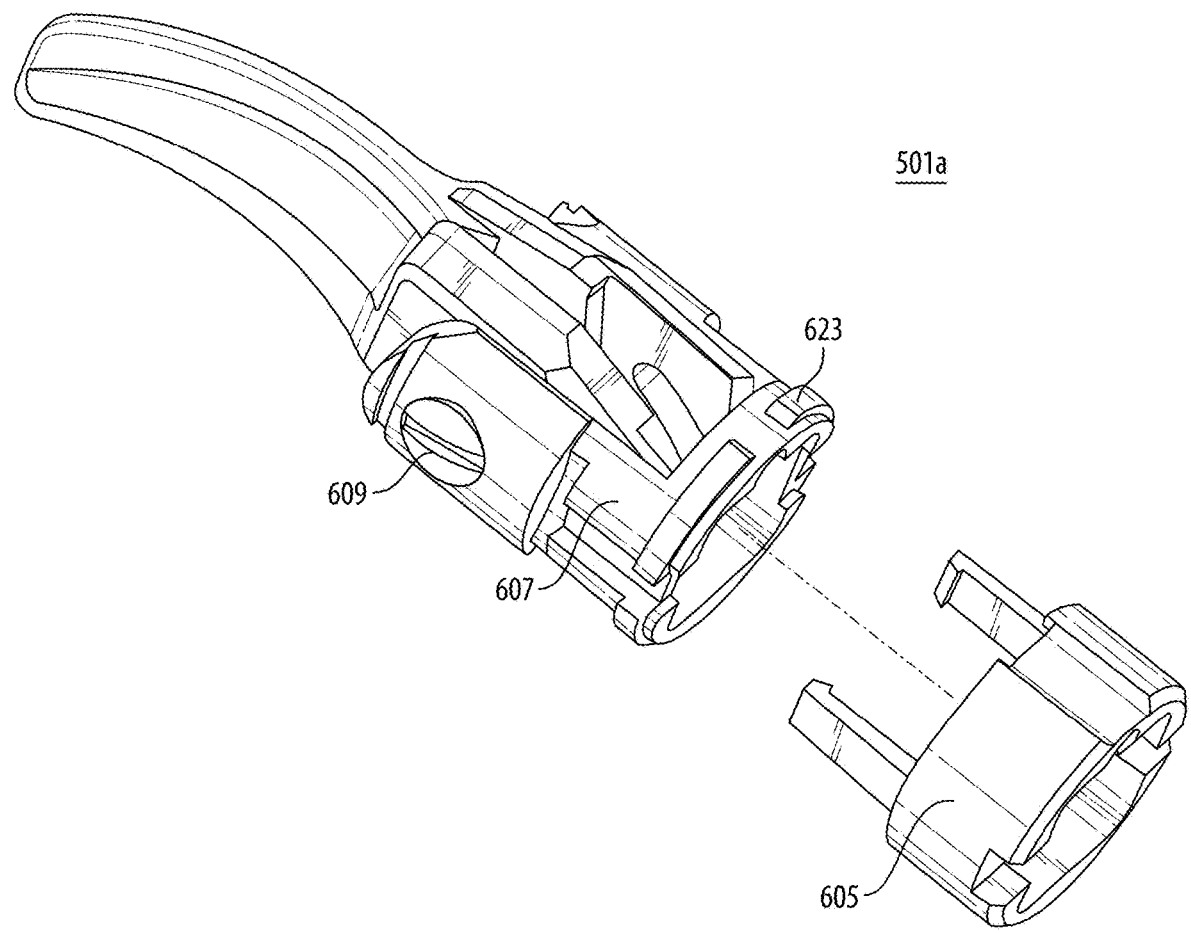
FIG. 6B is a partial exploded view of the embodiment of FIG. 6A.

FIGS. 6A and 6B show the embodiment of the disposable distal portion 501a of FIG. 5 separated from the base 501b. As shown, the disposable distal portion 501a can include a mount portion 605 configured to abut the base 501b, and a clevis 607 connected to the mount portion 605. The mount portion 605 can be a clip having one or more arrowhead or other type clip arms that interface with the clevis 607. The blades or jaws 105a, 105b can be mounted to the clevis 607 to pivot about a pivot joint 609 of the clevis 607.

Figure 7A:
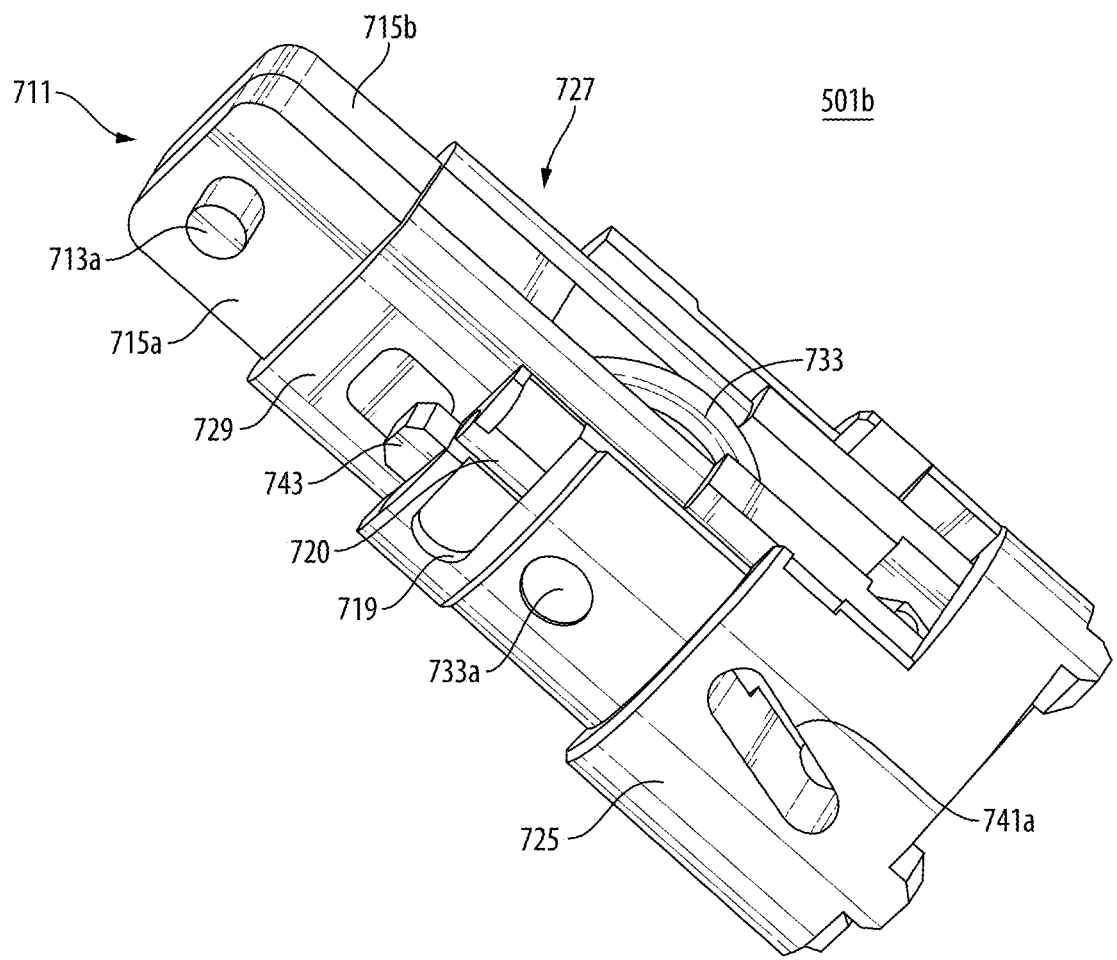
FIG. 7A is a perspective view of an embodiment of a base of the embodiment of FIG. 5.
Figure 7B:
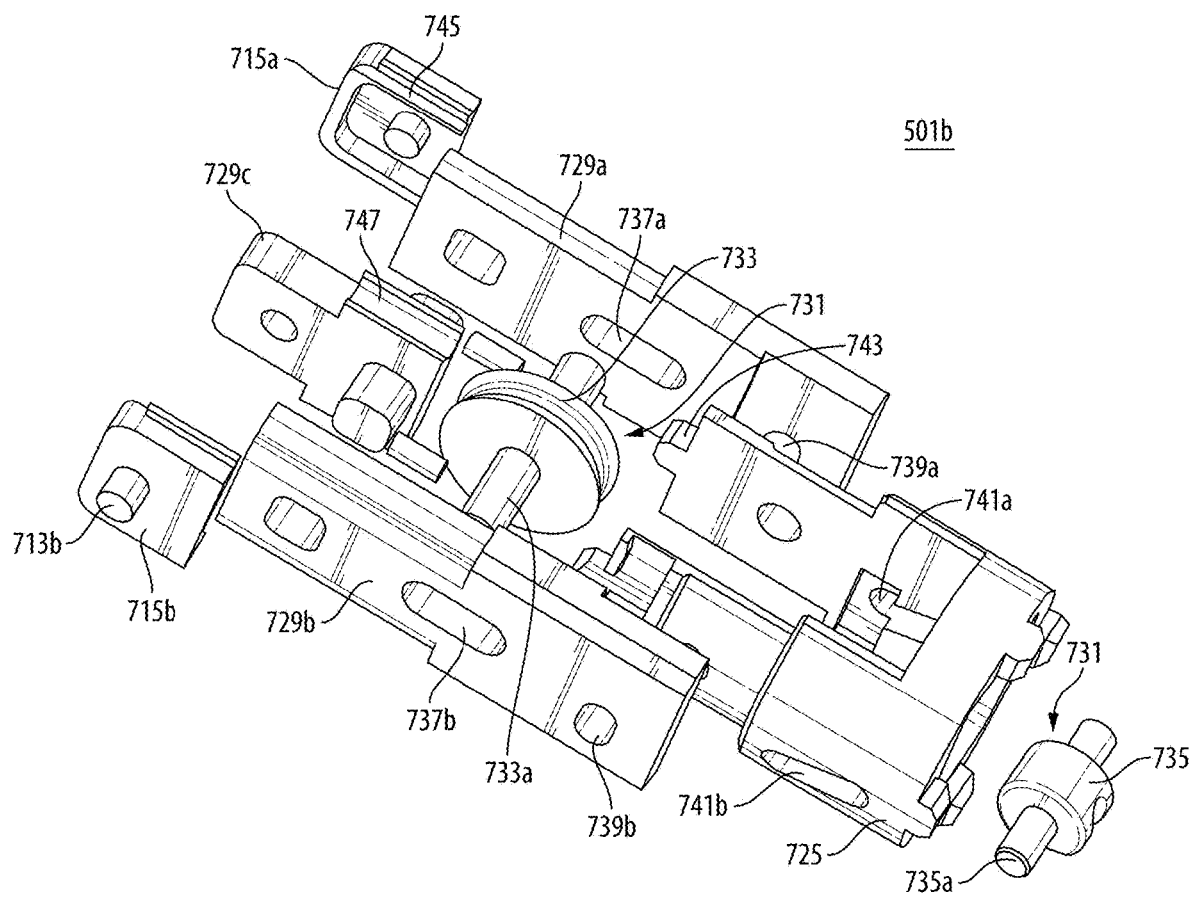
FIG. 7B is an exploded perspective view of the embodiment of FIG. 7A.

FIGS. 7A and 7B show the embodiment of the base of FIG. 5 separated from the disposable distal portion 501a. The base 501b can be configured to removably mechanically engage the blades or jaws 105a, 105b to actuate the blades or jaws 105a, 105b. For example, the base 501b can include a drive structure 711 configured to mechanically engage the blades or jaws 105a, 105b to actuate the blades or jaws 105a, 105b between an open and a closed position. The drive structure 711 can include a post 713a, 713b extending from each side (e.g., which can be formed of portions 715a, 715b).

Figure 8A:
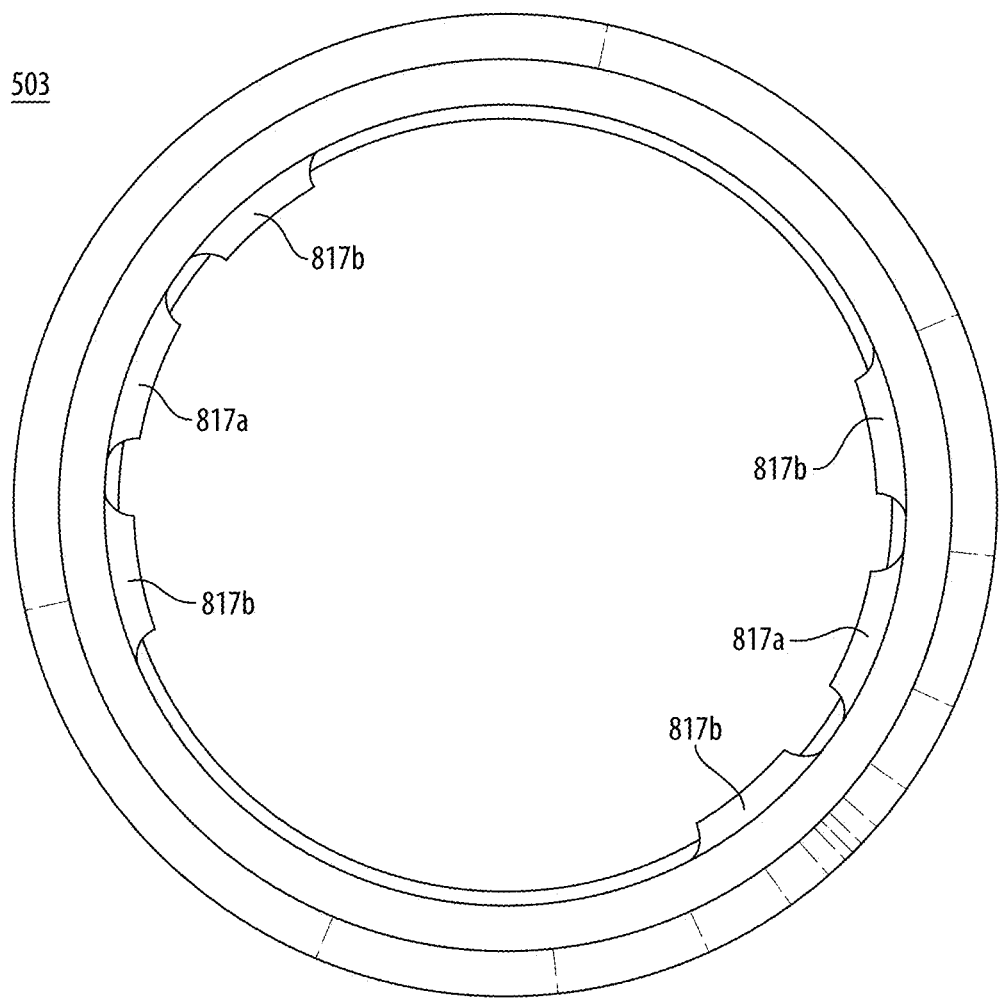
FIG. 8A is a plan view of the embodiment of a locking sleeve shown in FIG. 5A in accordance with this disclosure, shown having symmetric inner lock protrusions.
Figure 8B:
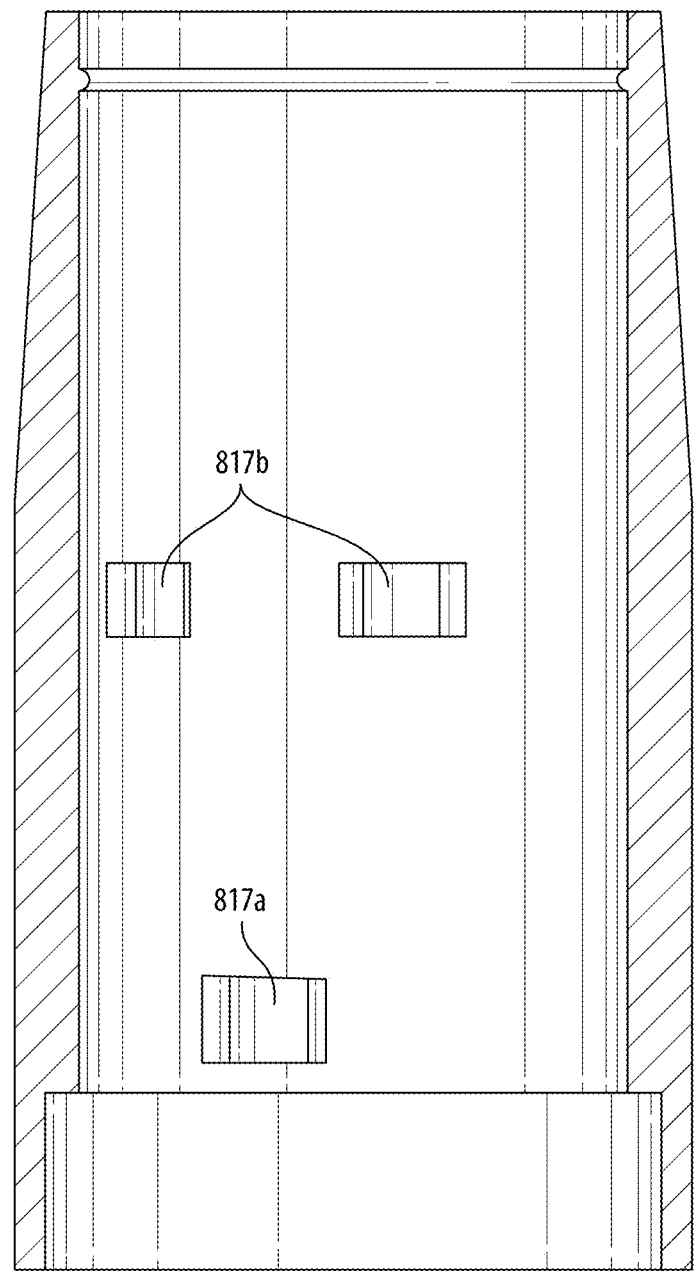
FIG. 8B is a cross-sectional elevation view of the embodiment of FIG. 8A, showing a group of inner lock protrusions.
Figure 8C:
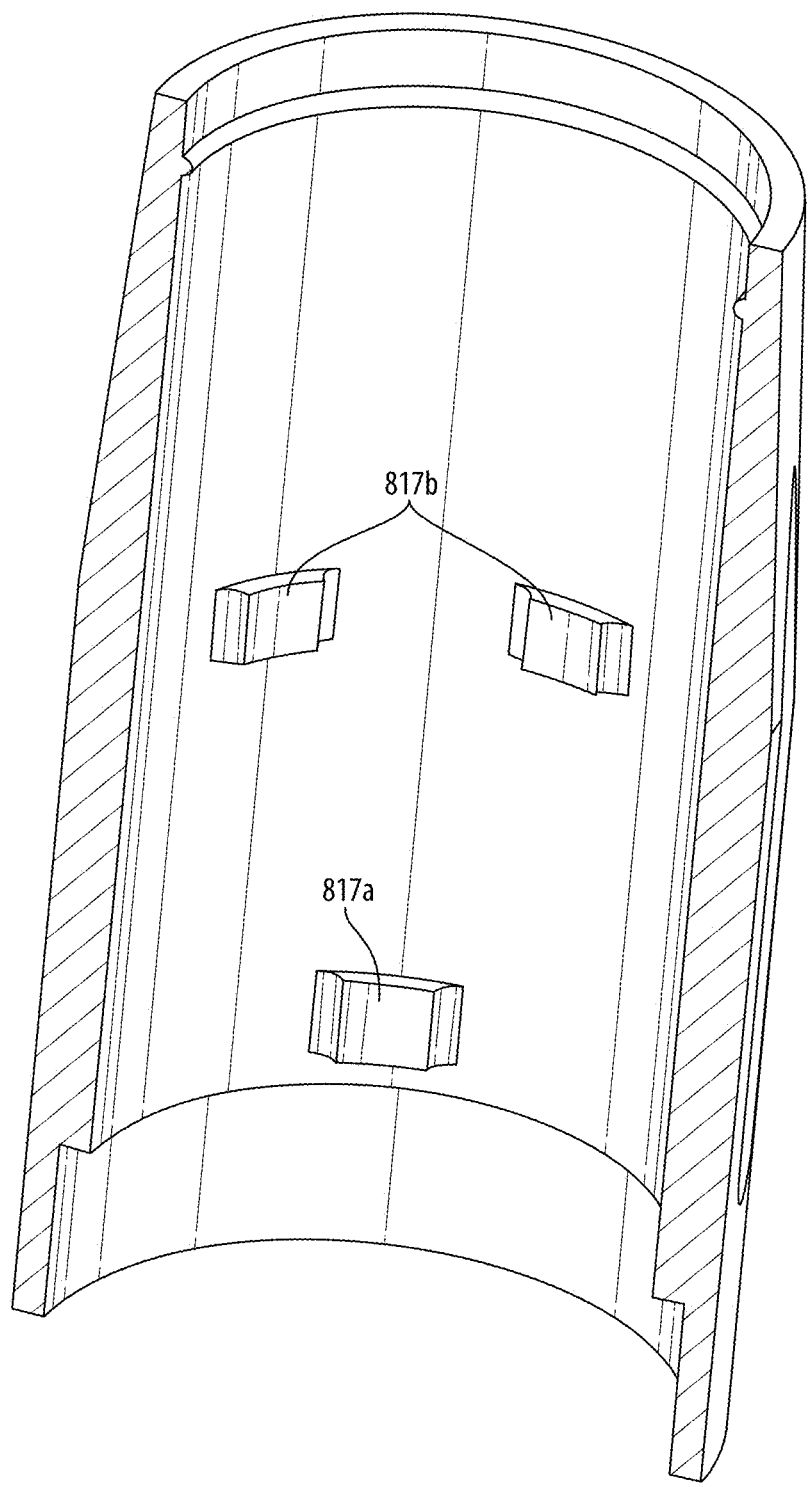
FIG. 8C is a cross-sectional perspective view of the embodiment of FIG. 8A.

FIGS. 8A-8C show the embodiment of a locking sleeve 503 shown in FIG. 5A. The disposable distal portion 501a and the base 501b can be configured to be selectively retained together by the locking sleeve 503. As shown, the locking sleeve 503 can include a plurality of lock protrusions 817a, 817b on an inner surface thereof. The locking sleeve 503 is shown having symmetric inner lock protrusions 817a, 817b, for example. The end effector 500 can further include the locking sleeve 503 configured to selectively lock the disposable distal portion 501a to the base 501b. The locking sleeve 503 can be made of a flexible or semi-rigid material (e.g., a non-conductive material such as silicone). The lock protrusions 817a, 817b can include a trapezoidal shape as shown (e.g., having a top surface and slanted or curved sides). Any other suitable shape to enable locking as disclosed herein is contemplated herein.

The base 501b can include one or more locking channels 719 (e.g., two symmetrically placed on each side 180 degrees apart). The locking channels 719 can include one or more bump protrusions (e.g., a smooth axially aligned pin) that create a barrier to be overcome by the proximal lock protrusions 817a when rotating into and/or out of the locking channels 719.

The disposable distal portion 501a can include one or more alignment channels 621 (e.g., two symmetrically placed on each side 180 degrees apart) defined through a lip 623 thereof (e.g., and through an outer portion of the mounting portion 605. Referring additionally to FIGS. 9A-9F, for example, one or more proximal lock protrusions 817a can be configured to be axially advanced through the alignment channels 621 to a position beyond the lip 623 and rotated into a respective locking channel 719 of the base 501b. Also, one or more distal inner stop protrusions 817b can be configured to axially engage the lip 623 to limit axial advancement of the sleeve 503 (e.g., as shown in FIGS. 9C and 9D) and to retain the disposable distal portion 501a to the base 510b when the sleeve 503 is rotated into a locked position (e.g., as shown in FIGS. 9D-9F) such that the one or more proximal lock protrusions 817a are within the one or more locking channels 719. The distal inner stop protrusions 817b can include a pair for each proximal lock protrusion 817a, the pair being at the same axial location but circumferentially spaced as shown (e.g., forming a T shaped outline with the proximal lock protrusion 817a as shown).

Figure 9A:
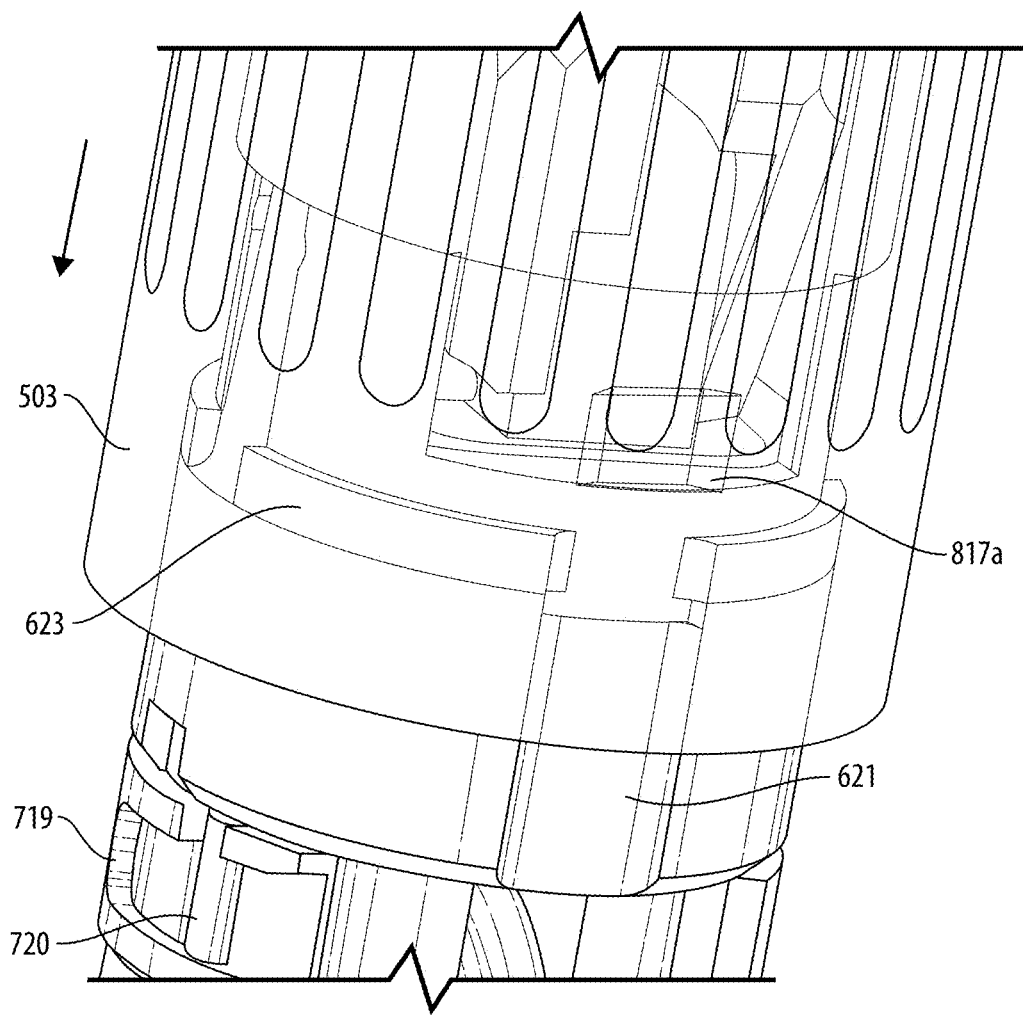
FIG. 9A shows the locking sleeve of FIG. 8A (shown in phantom for clarity) being axially advanced in a proximal direction over the mechanical assembly of FIG. 5B, shown having proximal inner lock protrusions of the locking sleeve aligned with respective alignment channels defined by the disposable distal portion.
Figure 9B:
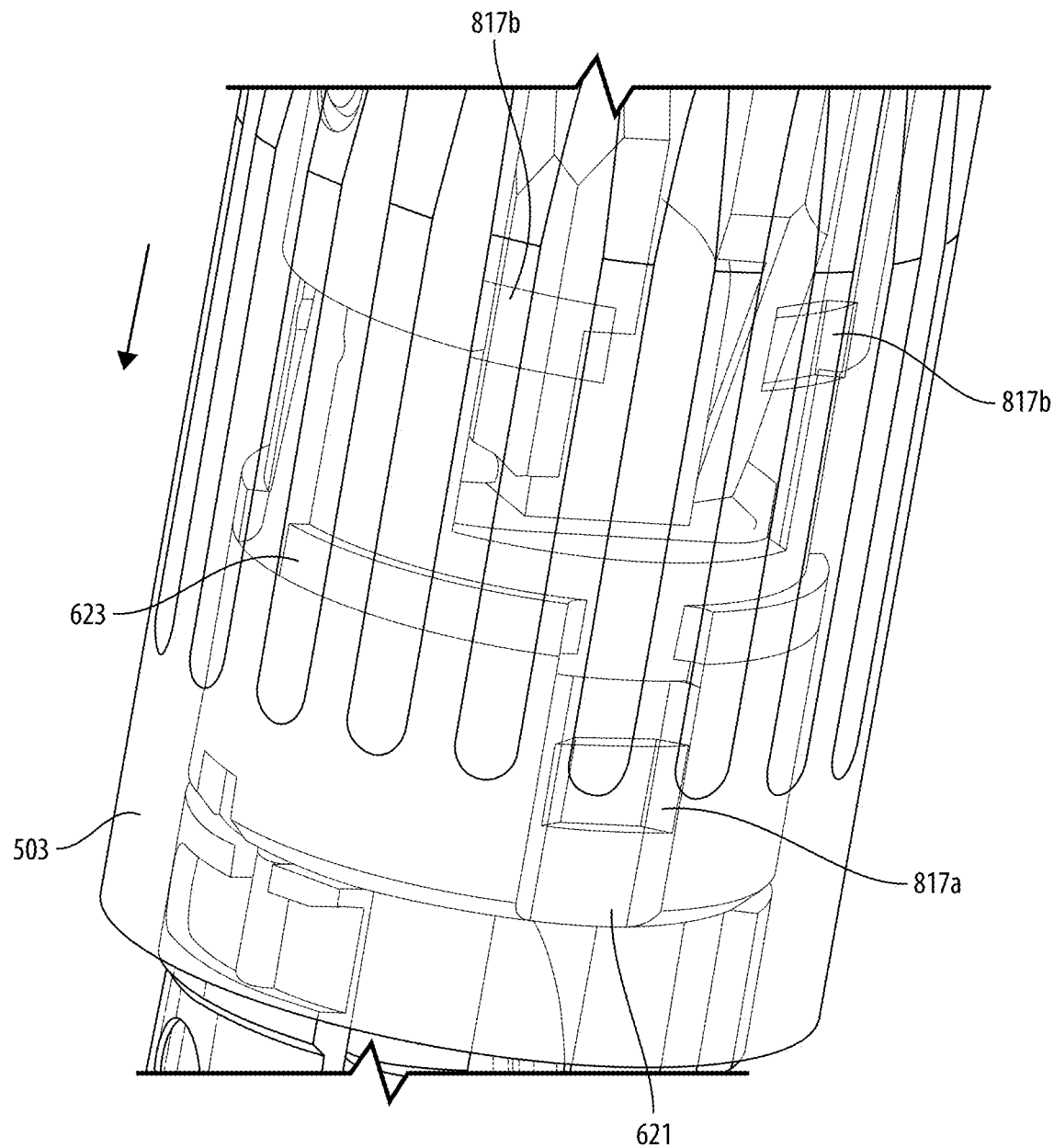
FIG. 9B shows the locking sleeve being axially advanced in the proximal direction over the disposable distal portion such that the proximal inner lock protrusions are within the respective alignment channels.
Figure 9C:
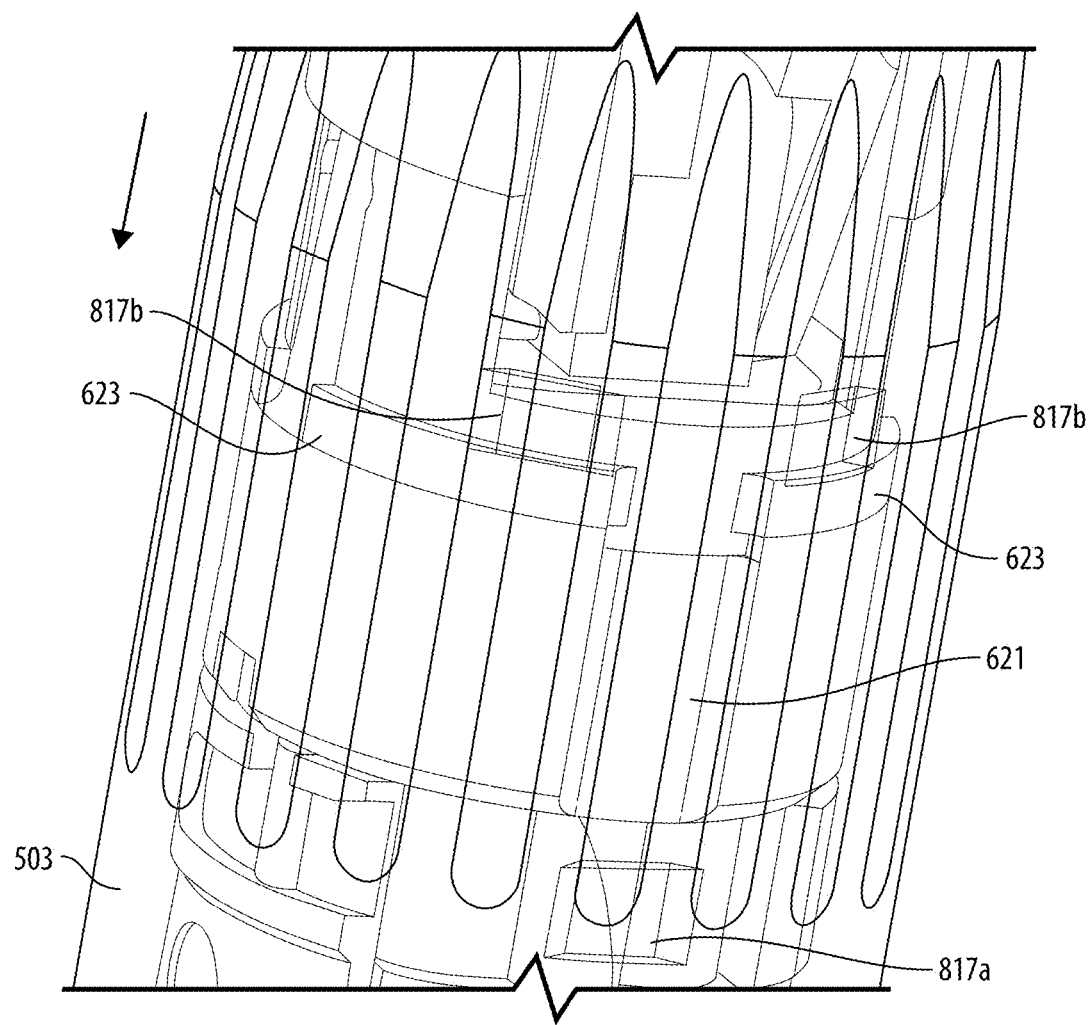
FIG. 9C shows the locking sleeve being axially advanced further such that the proximal inner lock protrusions are advanced proximally of the respective alignment channels of the disposable distal portion and such that distal inner stop protrusions of the locking sleeve abut a surface of the disposable distal portion to provide axial retention of the disposable distal portion to the base.
Figure 9D:
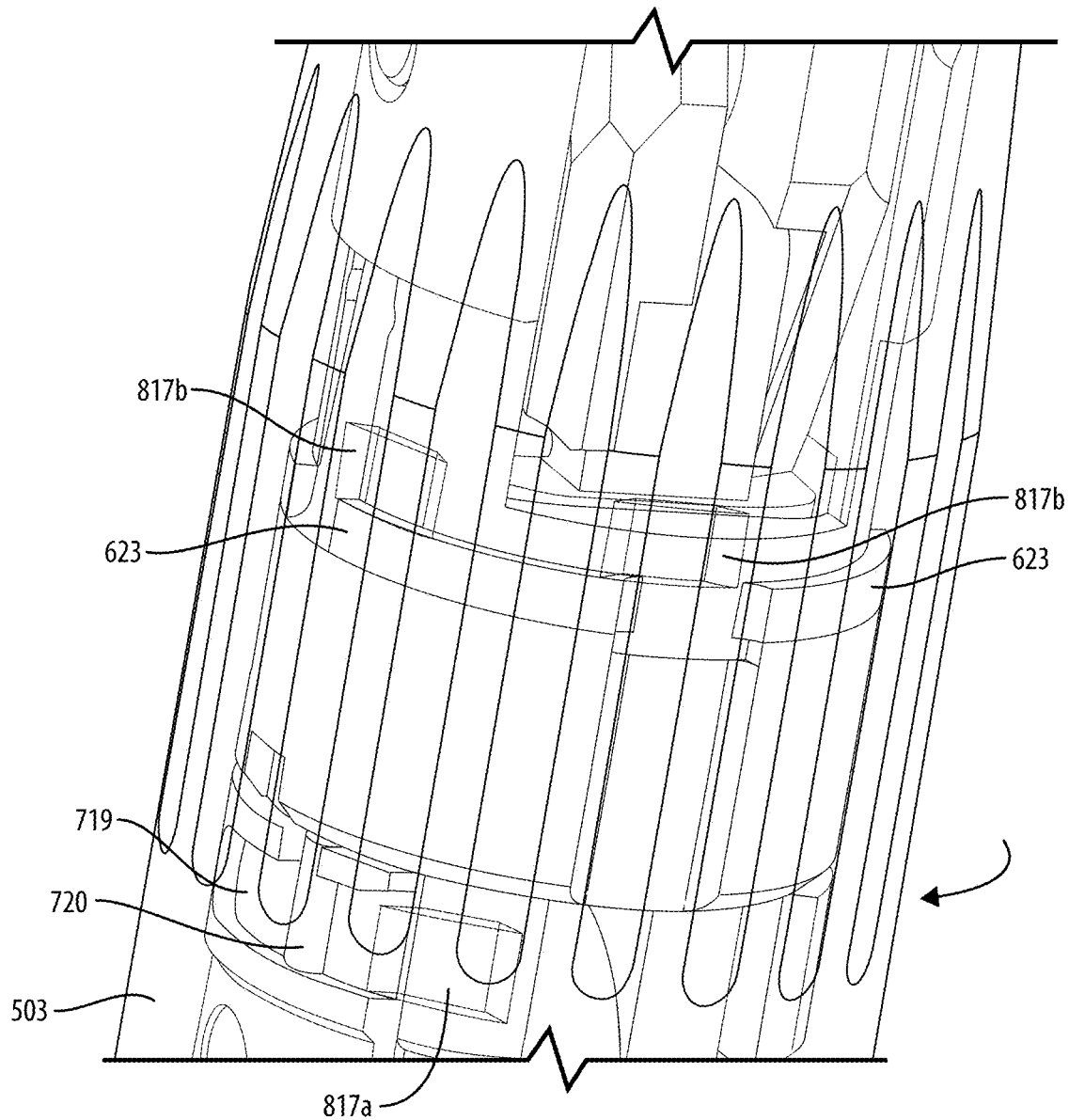
FIG. 9D shows the locking sleeve being rotated relative to the mechanical assembly such that the proximal inner lock protrusions are rotated toward respective lock channels defined by the base of the mechanical assembly.
Figure 9E:
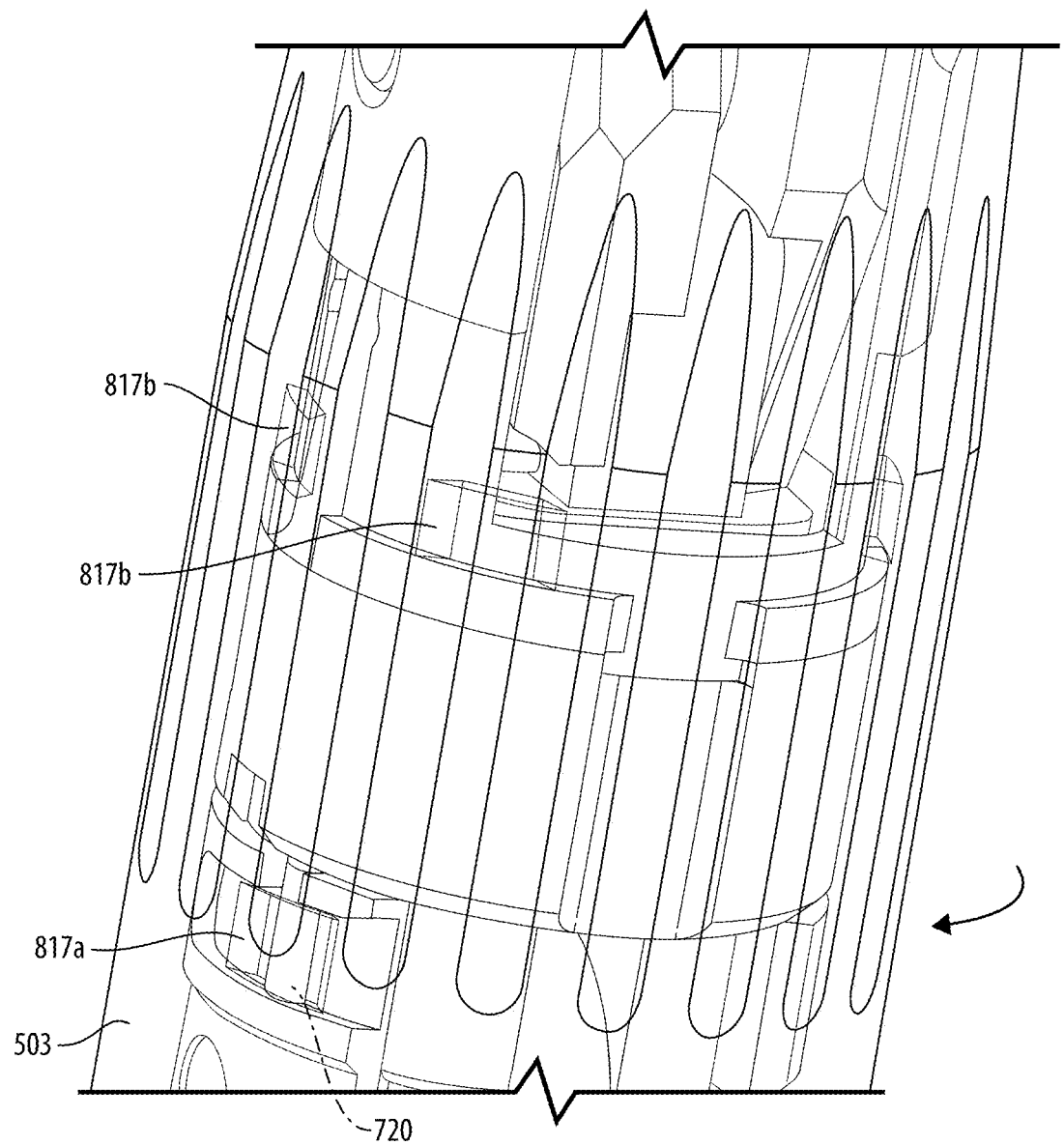
FIG. 9E shows the locking sleeve being rotated relative to the mechanical assembly such that the proximal inner lock protrusions are rotated further into the respective lock channels defined by the base of the mechanical assembly to move the proximal inner lock protrusions to a locked position wherein the proximal inner lock protrusions are retained by interaction with a lock structure of the base.
Figure 9F:
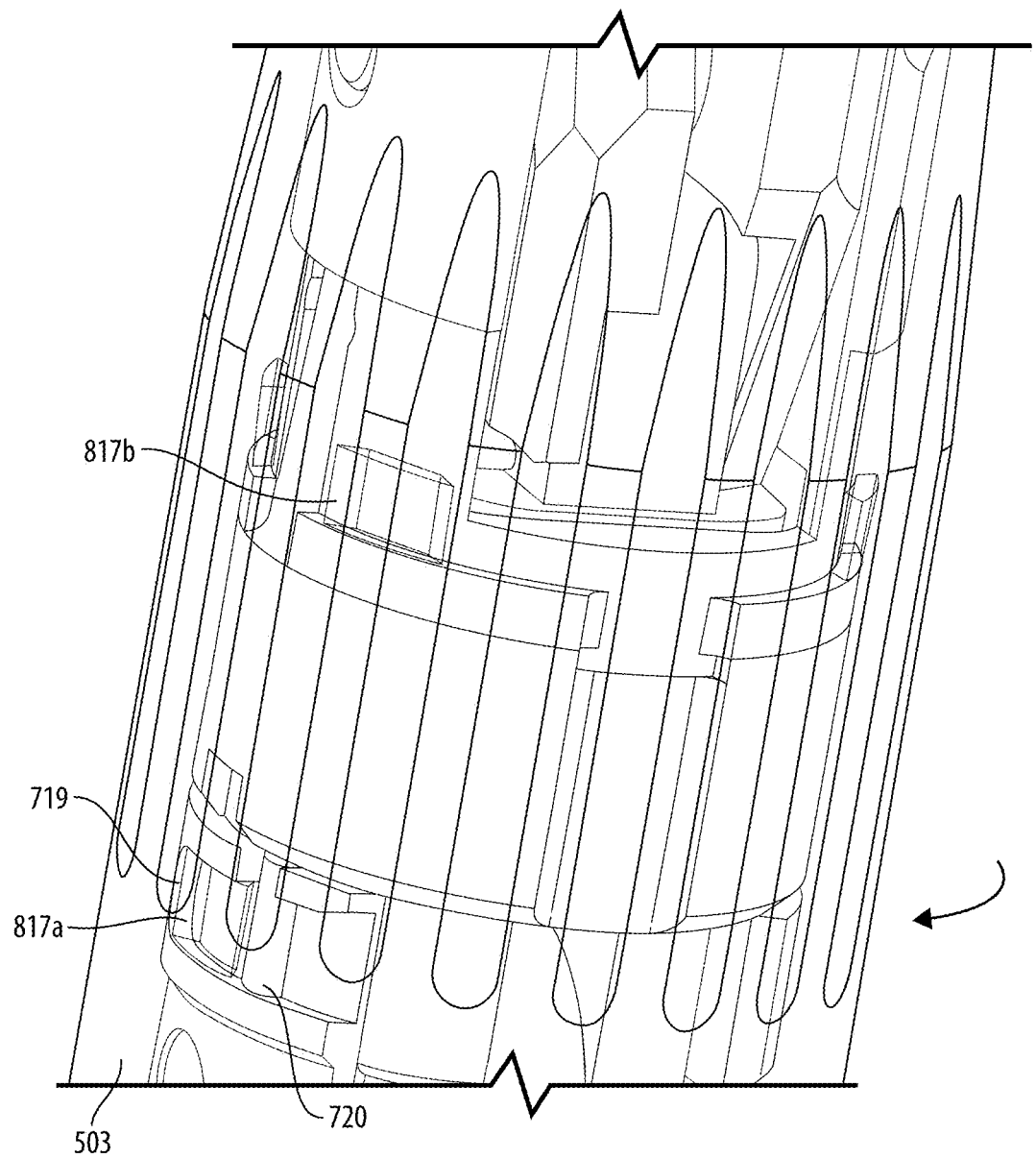
FIG. 9F shows the locking sleeve being rotated relative to the mechanical assembly such that the proximal inner lock protrusions are rotated to a locked position wherein the proximal inner lock protrusions are rotationally retained, and such that the distal inner stop protrusions are also axially retaining the disposable distal portion to the base.

FIG. 9A shows the locking sleeve 503 of FIG. 8A (shown in phantom for clarity) being axially advanced in a proximal direction over the mechanical assembly 501 of FIG. 5B. FIG. 9B shows the locking sleeve 503 being axially advanced in the proximal direction over the disposable distal portion 501a such that the proximal inner lock protrusions 817a are within the respective alignment channels 621. FIG. 9C shows the locking sleeve 503 being axially advanced further such that the proximal inner lock protrusions 817a are advanced proximally of the respective alignment channels 621 of the disposable distal portion 501a and such that distal inner stop protrusions 817b of the locking sleeve 503 abut a surface (e.g., the lip 623) of the disposable distal portion 501a to provide axial retention of the disposable distal portion 501a to the base 501b. FIG. 9D shows the locking sleeve 503 being rotated relative to the mechanical assembly 501 such that the proximal inner lock protrusions 817a are rotated toward respective lock channels 719 defined by the base 501b of the mechanical assembly 501. FIG. 9E shows the locking sleeve 503 being rotated relative to the mechanical assembly 501 such that the proximal inner lock protrusions 817a are rotated further into the respective lock channels 719 defined by the base 501b of the mechanical assembly 501 to move the proximal inner lock protrusions 817a to a locked position wherein the proximal inner lock protrusions 817a are retained by interaction with a lock structure (e.g., bump 720) of the base 501b. FIG. 9F shows the locking sleeve 503 being rotated relative to the mechanical assembly 501 such that the proximal inner lock protrusions 817a are rotated to a locked position wherein the proximal inner lock protrusions 817a are rotationally retained, and such that the distal inner stop protrusions 817b are also axially retaining the disposable distal portion 501a to the base 501b.

In certain embodiments, the base 501b can include a base clevis 725 and an actuation assembly 727 connected to the base clevis 725 and the drive structure 715 to actuate the drive structure 715 relative to the base clevis 725. The actuation assembly 727 can include an actuator housing 729 connected to the drive structure 715 (e.g., comprising portions 729a, 729b, and 729c). The actuation assembly 729 can also include a pulley assembly 731 within the actuator housing 729 and configured to move the actuator housing 729 relative to the base clevis 725.

In certain embodiments, the pulley assembly 731 can include a pulley 733 and an anchor 735. The pulley 733 can be pinned to the base clevis 725 via a pulley pin 733a (e.g., disposed in a pin hole of the base clevis 725 to only rotate relative to the base clevis 725). The pulley pin 733a can be disposed within an axial slot 737a, 737b of the actuator housing 729 to allow the actuator housing 729 to axially slide relative to the pulley 733. The anchor 735 can be configured to move relative to the pulley 733 between an open position of the blades or jaws 105a, 105b and a closed position of the blades or jaws 105a, 105b. The anchor 735 can be slidably connected via an anchor pin 735a to the actuator housing 729 at a radial slot 739a, 739b to translate relative to the actuator housing 729 in a radial direction orthogonal to the axial direction. In certain embodiments, the base clevis 725 can include a diagonal slot 741a, 741b configured to guide the anchor pin 735a within the radial slot 739a, 739b as the actuator housing 729 moves axially relative to the base clevis 725.

The anchor 735 can be configured to retain a first end of a first wire (not shown) that is wrapped around the pulley 733. The anchor 735 can be configured to retain a second end of a second wire (which can be the same wire as the first wire, or can be a different wire; not shown) such that pulling actuation on the first wire brings the anchor 735 closer to the pulley 733 thereby distally actuating the actuator housing 729, and pulling actuation on the second wire separates the pulley 733 and the anchor 735 thereby proximally actuating the actuator housing 729.

In certain embodiments, the base clevis 735 can be configured to abut the mount portion 605 and to orient the mount portion 605 rotationally relative to the base 501b (e.g., with one or more mount keys 743). In certain embodiments, the mount portion 605 and the base clevis 725 can include, e.g., be made of, a non-conductive material (e.g., rigid plastic). In certain embodiments, however, the base clevis 725 can include (e.g., be made of) a metal or alloy. In certain embodiments, the actuator housing 729 can include (e.g., be made of) a non-conductive material (e.g., rigid plastic). The drive structure 711 can include (e.g., be made of) a conductive material and can be configured to electrically connect to an electrical wire (e.g., mounted in a wire channel 745). The drive structure 711 can be attached to the actuator housing 729 in any suitable manner (e.g., pinned and/or otherwise fixed to the non-conductive core member 729c which can also form a wire guide channel 747).

Figure 10C:
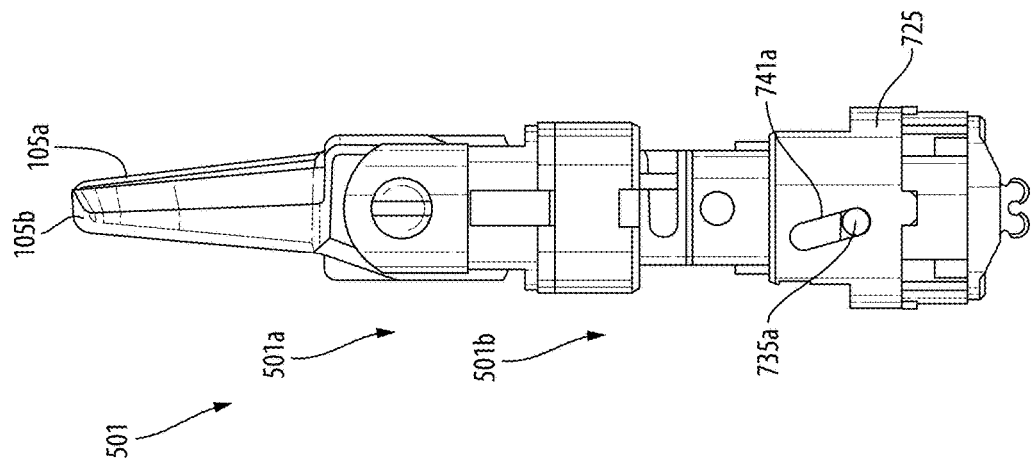
FIG. 10C is an elevation view of the mechanical assembly of FIG. 10A, shown in a closed position.
Figure 10B:
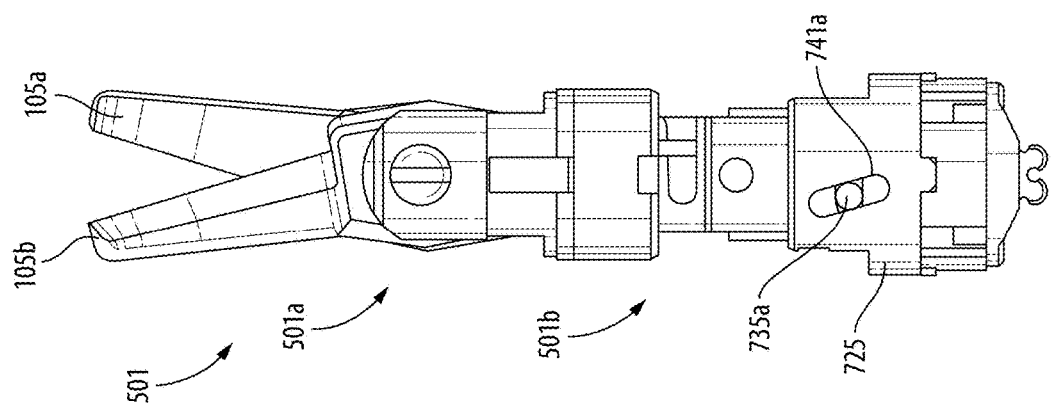
FIG. 10B is an elevation view of the mechanical assembly of FIG. 10A, shown in an intermediate position.
Figure 10A:
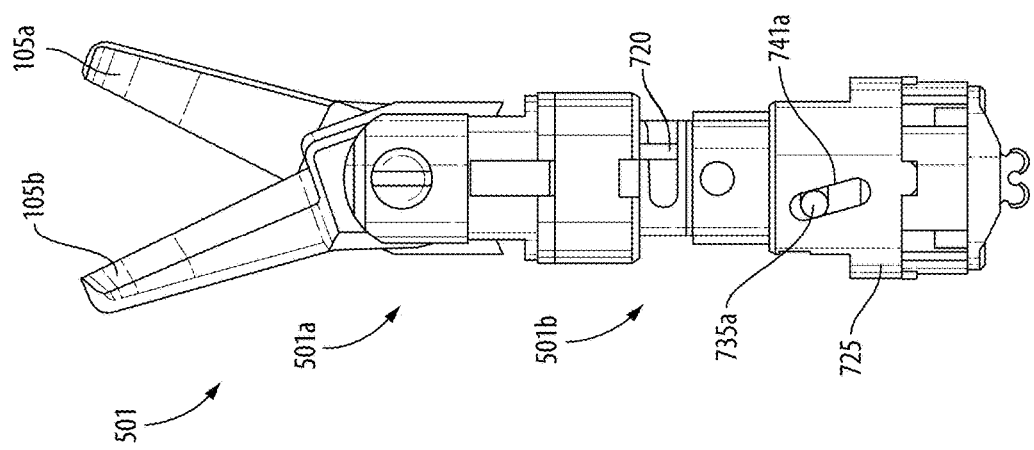
FIG. 10A is an elevation view of the mechanical assembly of FIG. 5B, shown in the open position.

FIGS. 10A-13C illustrate various views of the embodiment of FIG. 5A, shown in an open position, an intermediate position, and a closed position. FIG. 10A is an elevation view of the mechanical assembly 501 of FIG. 5B, shown in the open position. FIG. 10B is an elevation view of the mechanical assembly of FIG. 10A, shown in an intermediate position. FIG. 10C is an elevation view of the mechanical assembly of FIG. 10A, shown in a closed position.

Figure 11C:
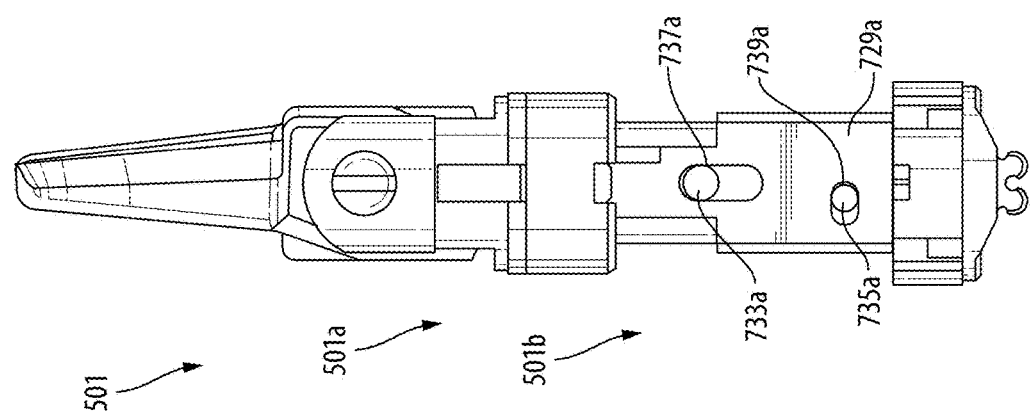
FIG. 11C is an elevation view of the mechanical assembly of FIG. 11A, shown in a closed position.
Figure 11B:
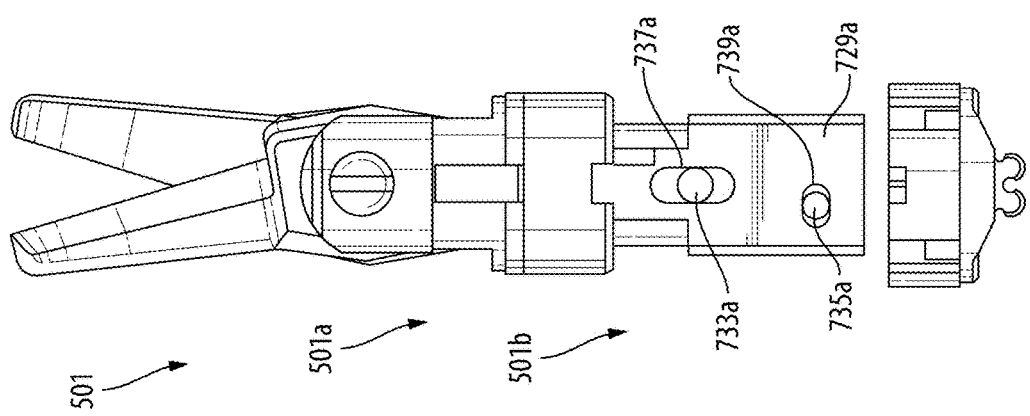
FIG. 11B is an elevation view of the mechanical assembly of FIG. 11A, shown in an intermediate position.
Figure 11A:
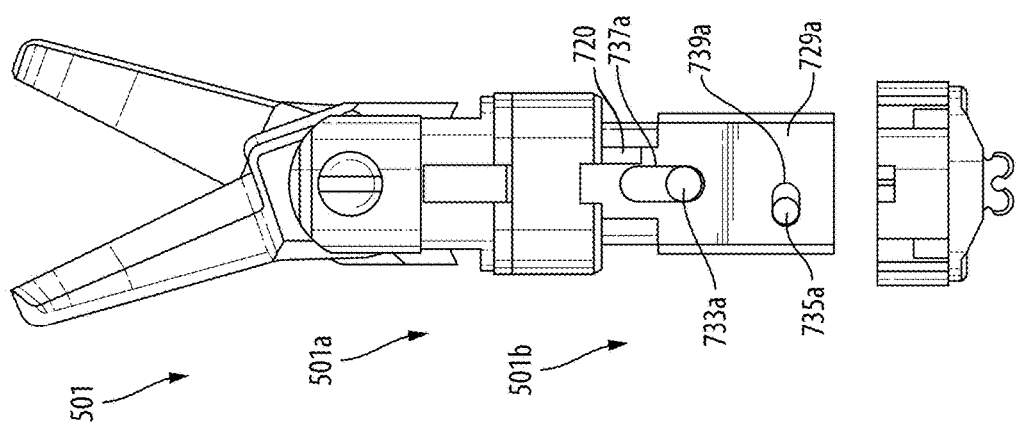
FIG. 11A is an elevation view of the mechanical assembly of FIG. 10A having a base clevis removed to illustrate the actuator housing, shown in the open position.

FIG. 11A is an elevation view of the mechanical assembly 501 of FIG. 10A showing the base clevis 725 removed to illustrate the actuator housing 729, shown in the open position. FIG. 11B is an elevation view of the mechanical assembly of FIG. 11A, shown in an intermediate position. FIG. 11C is an elevation view of the mechanical assembly of FIG. 11A, shown in a closed position.

Figure 12C:
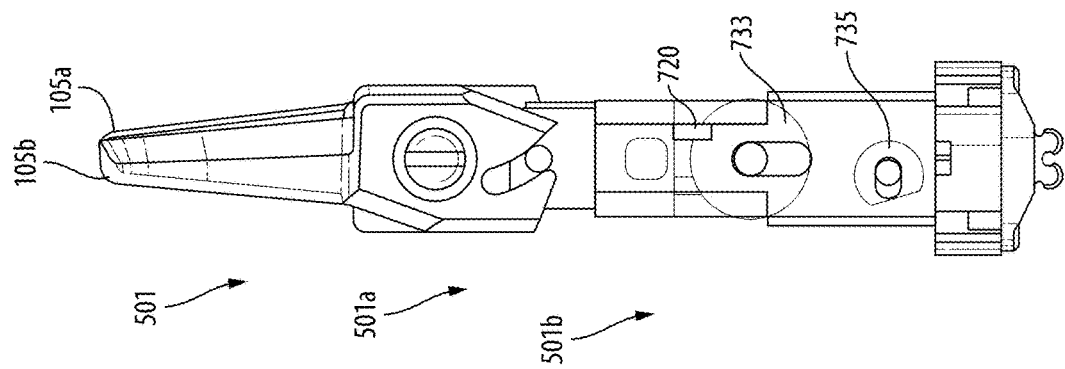
FIG. 12C is an elevation view of the mechanical assembly of FIG. 12A, shown in a closed position.
Figure 12B:
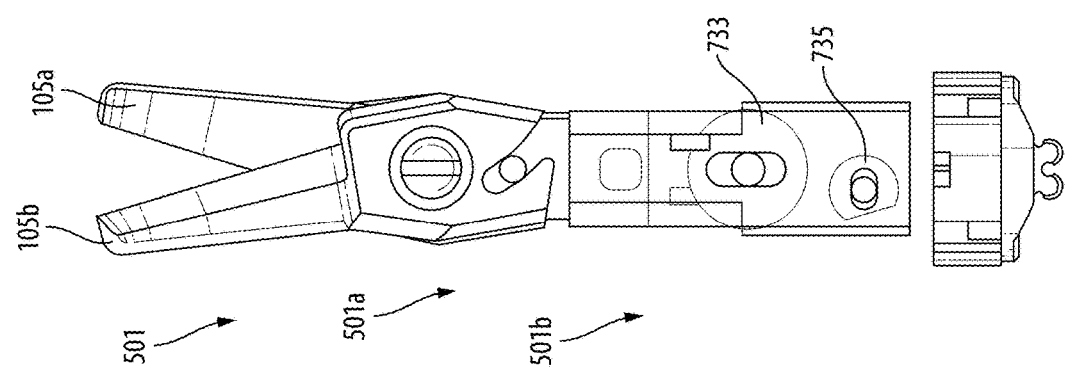
FIG. 12B is an elevation view of the mechanical assembly of FIG. 12A, shown in an intermediate position.
Figure 12A:
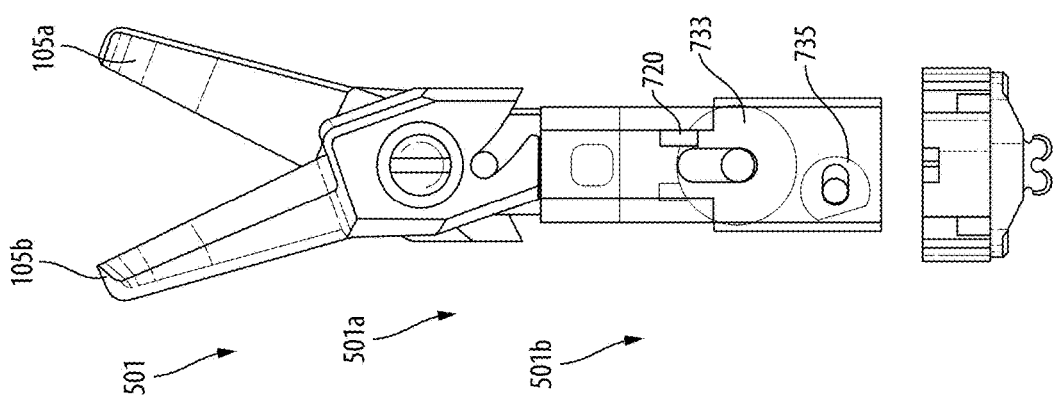
FIG. 12A is an elevation view of the mechanical assembly of FIG. 11A, further showing the actuator housing in phantom to illustrate an embodiment of a pulley arrangement, and shown in the open position.

FIG. 12A is an elevation view of the mechanical assembly 501 of FIG. 11A, further showing the actuator housing 729 in phantom to illustrate an embodiment of a pulley arrangement 731, and shown in the open position. FIG. 12B is an elevation view of the mechanical assembly of FIG. 12A, shown in an intermediate position. FIG. 12C is an elevation view of the mechanical assembly of FIG. 12A, shown in a closed position.

Figure 13C:
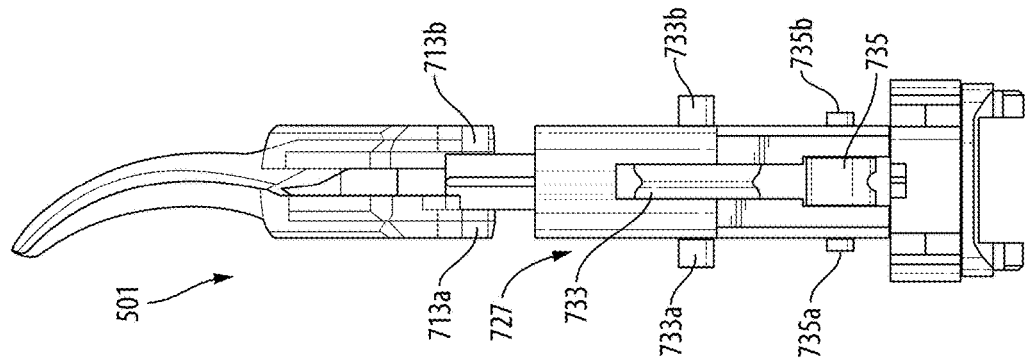
FIG. 13C is an elevation view of the mechanical assembly of FIG. 13A, shown in a closed position.
Figure 13B:
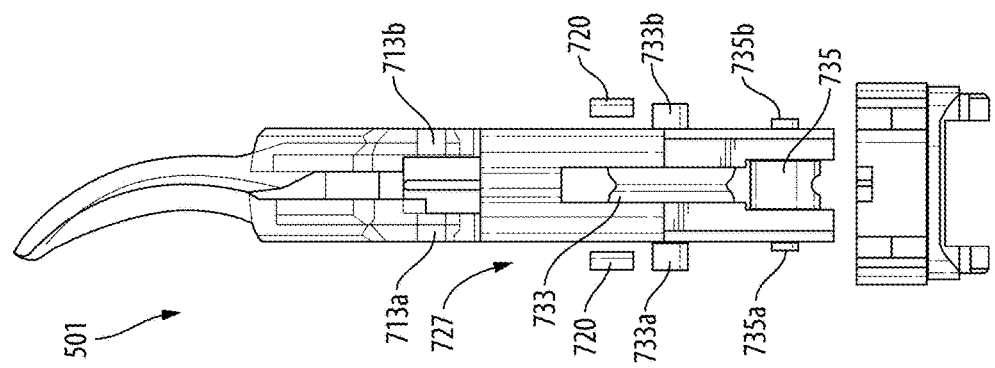
FIG. 13B is an elevation view of the mechanical assembly of FIG. 13A, shown in an intermediate position.
Figure 13A:
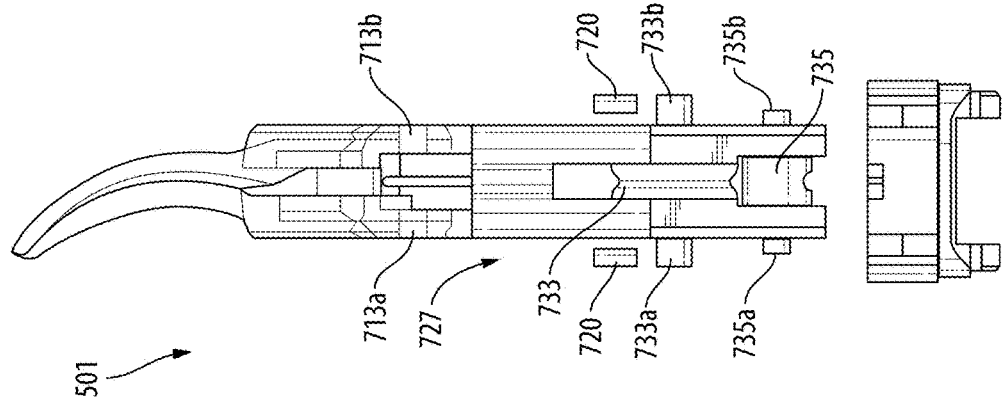
FIG. 13A is an elevation view of the mechanical assembly of FIG. 12A, shown orthogonal to the view of FIG. 12A, further showing the blades in phantom to illustrate actuation of the blades via actuator posts, and showing the assembly in the open position.

FIG. 13A is an elevation view of the mechanical assembly 501 of FIG. 12A, shown orthogonal to the view of FIG. 12A, further showing the blades 105a, 105b in phantom to illustrate actuation of the blades via actuator posts 713a, 713b, and showing the assembly in the open position. FIG. 13B is an elevation view of the mechanical assembly of FIG. 13A, shown in an intermediate position. FIG. 13C is an elevation view of the mechanical assembly of FIG. 13A, shown in a closed position.

Figure 14:
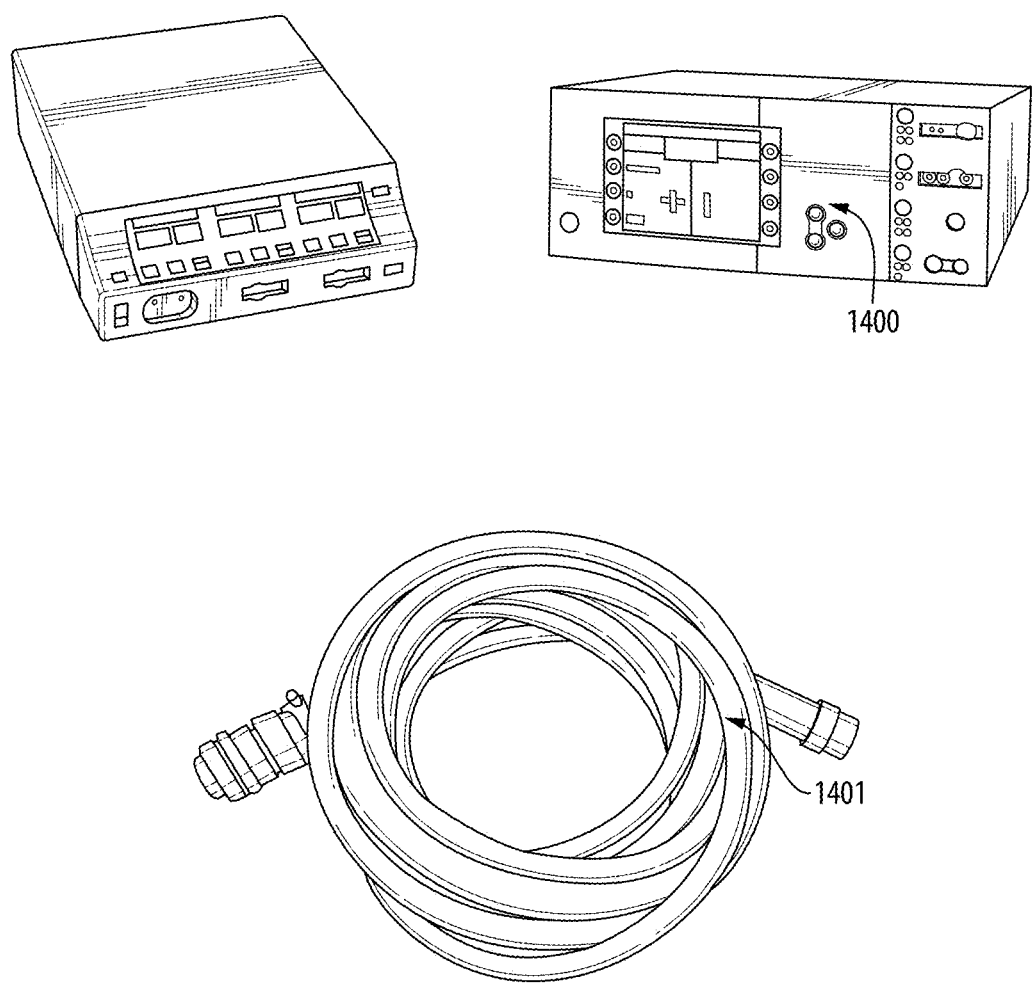
FIG. 14 is an embodiment of electrosurgical unit in accordance with this disclosure.

In certain embodiments, referring additionally to FIG. 14, the monopolar energy surgical instrument 400 is configured to be used with an electrosurgical unit (ESU) 1400 (e.g., as shown in FIG. 14) for transferring energy to the surgical target. The ESU 1400 is connected to a patient cart of a robotic surgical system (not shown) by an energy activation cable 1401. Any suitable ESU models and the corresponding ESU cable are contemplated herein.

In accordance with at least one aspect of this disclosure, a medical device (e.g., surgical instrument 400 for a robotic medical system) can include an adapter (e.g., adapter 401) configured to connect to and be actuated by a robotic surgical system. The medical device (e.g., surgical instrument 400) can include an elongate member (e.g., shaft 403) extending from the adapter (e.g., adapter 401). The elongate member (e.g., shaft 403) can be configured to be positioned as a function of the actuation of the adapter (e.g., adapter 401). For example, the elongate member (e.g., shaft 403) can include one or more wires therein and a flexible body to allow steering of the elongate member and/or a distal end thereof. The medical device (e.g., instrument 400) can include an end effector (e.g., end effector 407, such as end effector 100, 500) connected to the elongate member (e.g., shaft 403). In certain embodiments, the elongate member (e.g., shaft 403) can include or be connected to one or more bending segments (e.g., segments 405). The end effector (e.g., end effector 407) can be attached to a distal end of the one or more bending segments (e.g., segments 405).

The end effector (e.g., end effector 407) can be any suitable embodiment of an end effector as disclosed herein, e.g., as described above. For example, the end effector (e.g., end effector 407) can include a base portion and a disposable distal portion removably connected to the base.

In accordance with at least one aspect of this disclosure a method for operating an end effector for a minimally invasive medical device can include using an end effector in a medical procedure, detaching a first disposable distal portion of the end effector from a base of the end effector, and attaching a second disposable distal portion to the base of the end effector to replace the first distal portion. In certain embodiments, the method can include reusing the end effector having the second disposable distal portion in another medical procedure. The method can include any other suitable method(s) and/or portion(s) thereof.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. An end effector for a minimally invasive medical device, comprising:
   a base configured to attach to a distal end of a shaft; and
   a disposable distal portion configured to removably attach to the base to be disposed of after use,
   wherein the disposable distal portion includes an electrically conductive material for an electrosurgical procedure, wherein the disposable distal portion is electrically connected to the base when removably attached to the base,
   wherein the disposable distal portion is or includes blades or jaws including a conductive material to provide electrosurgical energy to tissue,
   wherein the disposable distal portion includes:
      a mount portion configured to abut the base; and
      a clevis connected to the mount portion, wherein the blades or jaws are mounted to the clevis to pivot about a pivot joint of the clevis,
   wherein the base is configured to removably mechanically engage the blades or jaws to actuate the blades or jaws,
   wherein the base includes a drive structure configured to mechanically engage the blades or jaws to actuate the blades or jaws between an open and a closed position,
   wherein the clevis further comprises a non-conductive material, and the mount portion further comprises a non-conductive center post configured to mechanically connect the blades or jaws to the drive structure to actuate the blades or jaws between the open and the closed position,
   wherein the disposable distal portion and the base are configured to be selectively axially retained together by a locking sleeve, wherein the locking sleeve is configured to selectively lock the disposable distal portion to the base, and
   wherein the base includes one or more locking channels, wherein the disposable distal portion includes one or more alignment channels defined through a lip, wherein the locking sleeve includes a plurality of lock protrusions on an inner surface thereof, one or more proximal lock protrusions are configured to be axially advanced through the alignment channels beyond the lip and rotated into a respective locking channel, wherein one or more distal inner stop protrusions are configured to axially engage the lip to limit axial advancement of the sleeve and to retain the disposable distal portion to the base when the sleeve is rotated into a locked position such that the one or more proximal lock protrusions are within the one or more locking channels.

2. The end effector of claim 1, wherein the base includes a base clevis and an actuation assembly connected to the base clevis and the drive structure to actuate the drive structure relative to the base clevis.

3. The end effector of claim 2, wherein the actuation assembly includes:
   an actuator housing connected to the drive structure; and
   a pulley assembly within the actuator housing and configured to move the actuator housing relative to the base clevis.

4. The end effector of claim 3, wherein the pulley assembly includes a pulley and an anchor, wherein the pulley is pinned to the base clevis via a pulley pin, wherein the pulley pin is disposed within an axial slot of the actuator housing to allow the actuator housing to axially slide relative to the pulley, wherein the anchor is configured to move relative to the pulley between an open position of the blades or jaws and a closed position of the blades or jaws.

5. The end effector of claim 4, wherein the anchor is slidably connected via an anchor pin to the actuator housing at a radial slot to translate relative to the actuator housing in a radial direction orthogonal to the axial direction.

6. The end effector of claim 5, wherein the base clevis includes a diagonal slot configured to guide the anchor pin within the radial slot as the actuator housing moves axially relative to the base clevis.

7. The end effector of claim 6, wherein the anchor is configured to retain a first end of a first wire that is wrapped around the pulley, wherein the anchor is configured to retain a second end of a second wire such that pulling actuation on the first wire brings the anchor closer to the pulley thereby distally actuating the actuator housing, and pulling actuation on the second wire separates the pulley and the anchor thereby proximally actuating the actuator housing.

8. The end effector of claim 7, wherein the base clevis is configured to abut the mount portion and to orient the mount portion rotationally relative to the base.

9. The end effector of claim 8, wherein the mount portion, the base clevis and the actuator housing comprises a non-conductive material respectively, and wherein the drive structure comprises a conductive material and configured to electrically connect to an electrical wire.

10. A minimally-invasive medical device, comprising:
   an adapter configured to connect to and be actuated by a robotic surgical system;
   an elongate member extending from the adapter, the elongate member configured to be positioned as a function of the actuation of the adapter; and
   an end effector connected to the elongate member, the end effector comprising:
      a base configured to attach to a distal end of a shaft; and
      a disposable distal portion configured to removably attach to the base to be disposed of after use,
   wherein the disposable distal portion includes an electrically conductive material for an electrosurgical procedure, wherein the disposable distal portion is electrically connected to the base when removably attached to the base, wherein the disposable distal portion is or includes blades or jaws including a conductive material to provide electrosurgical energy to tissue, wherein the disposable distal portion includes:
   a mount portion configured to abut the base; and
   a clevis connected to the mount portion, wherein the blades or jaws are mounted to the clevis to pivot about a pivot joint of the clevis, wherein the base is configured to removably mechanically engage the blades or jaws to actuate the blades or jaws, wherein the base includes a drive structure configured to mechanically engage the blades or jaws to actuate the blades or jaws between an open and a closed position, wherein the clevis further comprises a non-conductive material, and the mount portion further comprises a non-conductive center post configured to mechanically connect the blades or jaws to the drive structure to actuate the blades or jaws between the open and the closed position, wherein the disposable distal portion and the base are configured to be selectively axially retained together by a locking sleeve, wherein the locking sleeve is configured to selectively lock the disposable distal portion to the base, and wherein the base includes one or more locking channels, wherein the disposable distal portion includes one or more alignment channels defined through a lip, wherein the locking sleeve includes a plurality of lock protrusions on an inner surface thereof, one or more proximal lock protrusions are configured to be axially advanced through the alignment channels beyond the lip and rotated into a respective locking channel, wherein one or more distal inner stop protrusions are configured to axially engage the lip to limit axial advancement of the sleeve and to retain the disposable distal portion to the base when the sleeve is rotated into a locked position such that the one or more proximal lock protrusions are within the one or more locking channels.

11. The medical device of claim 10, wherein the base includes a base clevis and an actuation assembly connected to the base clevis and the drive structure to actuate the drive structure relative to the base clevis.

12. The medical device of claim 11, wherein the actuation assembly includes:
   an actuator housing connected to the drive structure; and
   a pulley assembly within the actuator housing and configured to move the actuator housing relative to the base clevis.

13. The medical device of claim 12, wherein the pulley assembly includes a pulley and an anchor, wherein the pulley is pinned to the base clevis via a pulley pin, wherein the pulley pin is disposed within an axial slot of the actuator housing to allow the actuator housing to axially slide relative to the pulley, wherein the anchor is configured to move relative to the pulley between an open position of the blades or jaws and a closed position of the blades or jaws.

14. The medical device of claim 13, wherein the anchor is slidably connected via an anchor pin to the actuator housing at a radial slot to translate relative to the actuator housing in a radial direction orthogonal to the axial direction.

15. The medical device of claim 14, wherein the base clevis includes a diagonal slot configured to guide the anchor pin within the radial slot as the actuator housing moves axially relative to the base clevis.

16. The medical device of claim 15, wherein the anchor is configured to retain a first end of a first wire that is wrapped around the pulley, wherein the anchor is configured to retain a second end of a second wire such that pulling actuation on the first wire brings the anchor closer to the pulley thereby distally actuating the actuator housing, and pulling actuation on the second wire separates the pulley and the anchor thereby proximally actuating the actuator housing.

17. The medical device of claim 16, wherein the base clevis is configured to abut the mount portion and to orient the mount portion rotationally relative to the base.

18. The medical device of claim 17, wherein the mount portion, the base clevis and the actuator housing comprises a non-conductive material respectively, and wherein the drive structure comprises a conductive material and configured to electrically connect to an electrical wire.

* * * * *